United States Patent
Liu et al.

(10) Patent No.: US 9,090,568 B2
(45) Date of Patent: Jul. 28, 2015

(54) QUINAZOLINEDIONES AND THEIR USE

(75) Inventors: Dong Liu, Bridgewater, NJ (US);
Minsheng Zhang, Greenbrook, NJ (US);
Kan He, Montgomery, NJ (US);
Lianshan Zhang, West Windsor, NJ (US)

(73) Assignee: IMPACT Therapeutics, Inc., Ninjing, Jiangsu Province (CN)

( * ) Notice: Subject to any disclaimer, the term of this patent is extended or adjusted under 35 U.S.C. 154(b) by 0 days.

(21) Appl. No.: 14/004,633

(22) PCT Filed: Mar. 12, 2012

(86) PCT No.: PCT/US2012/028698
§ 371 (c)(1),
(2), (4) Date: Oct. 17, 2013

(87) PCT Pub. No.: WO2012/125521
PCT Pub. Date: Sep. 20, 2012

(65) Prior Publication Data
US 2014/0031358 A1    Jan. 30, 2014

Related U.S. Application Data

(60) Provisional application No. 61/452,360, filed on Mar. 14, 2011.

(51) Int. Cl.
| | |
|---|---|
| C07D 239/96 | (2006.01) |
| C07D 239/80 | (2006.01) |
| C07D 401/10 | (2006.01) |
| C07D 401/12 | (2006.01) |
| C07D 401/14 | (2006.01) |
| C07D 403/10 | (2006.01) |
| C07D 403/12 | (2006.01) |
| C07D 405/12 | (2006.01) |
| C07D 413/12 | (2006.01) |
| C07D 471/04 | (2006.01) |
| C07D 487/04 | (2006.01) |

(52) U.S. Cl.
CPC ............ *C07D 239/96* (2013.01); *C07D 239/80* (2013.01); *C07D 401/10* (2013.01); *C07D 401/12* (2013.01); *C07D 401/14* (2013.01); *C07D 403/10* (2013.01); *C07D 403/12* (2013.01); *C07D 405/12* (2013.01); *C07D 413/12* (2013.01); *C07D 471/04* (2013.01); *C07D 487/04* (2013.01)

(58) Field of Classification Search
CPC ........................... C07D 239/06; C07D 401/14
USPC ................. 514/266.2; 544/283, 284
See application file for complete search history.

(56) References Cited

U.S. PATENT DOCUMENTS

| | | | |
|---|---|---|---|
| 4,405,623 | A | 9/1983 | Ishikawa et al. |
| 4,797,403 | A | 1/1989 | Lowe, III |
| 6,201,121 | B1 | 3/2001 | Kamiya et al. |
| 6,344,559 | B1 | 2/2002 | Omori et al. |
| 2005/0159431 | A1 | 7/2005 | Albrecht et al. |
| 2008/0039480 | A1 | 2/2008 | Kennis et al. |
| 2014/0023642 | A1 | 1/2014 | Cai et al. |

FOREIGN PATENT DOCUMENTS

| | | |
|---|---|---|
| CN | 1980913 A | 6/2007 |
| DE | 26 52 144 A1 | 5/1978 |
| EP | 0 795 548 A1 | 9/1997 |
| JP | 10-195058 A | 7/1998 |
| JP | 2001-302515 A | 10/2001 |
| JP | 2002-284699 A | 10/2002 |
| JP | 2007-137818 A | 6/2007 |
| WO | WO 98/27975 A1 | 7/1998 |
| WO | WO 02/102793 A2 | 12/2002 |
| WO | WO 2006/003148 A1 | 1/2006 |
| WO | WO 2008/105470 A1 | 12/2008 |

(Continued)

OTHER PUBLICATIONS

Pinedo et al (2000).*

(Continued)

*Primary Examiner* — Paul V Ward
(74) *Attorney, Agent, or Firm* — Sterne, Kessler, Goldstein & Fox P.L.L.C.

(57) ABSTRACT

The present invention discloses compounds of formula (I), or pharmaceutically acceptable salts or prodrugs thereof, which inhibit the poly(ADP-ribose) polymerases (PARP) and therefore are useful for treating diseases, disorders, and conditions related to PARP. The present invention also discloses pharmaceutical compositions comprising a compound of formula (I), and methods of using such compounds to inhibit PARP enzymes, and to treat diseases, disorders, and conditions related to PARP.

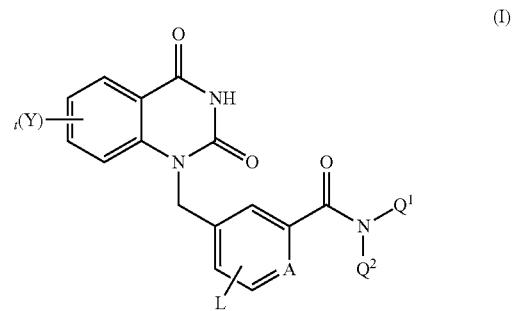

16 Claims, No Drawings

(56) References Cited

FOREIGN PATENT DOCUMENTS

| WO | WO 2008/150470 A1 | 12/2008 |
| WO | WO 2009/027730 A1 | 3/2009 |
| WO | WO 2009/118384 A1 | 10/2009 |

OTHER PUBLICATIONS

McMahon et al (2000).*

International Search Report, International Application No. PCT/US2012/028698, Jul. 5, 2012, 1 page.

Stephen M. Berge et al., "Pharmaceutical Salts," Journal of Pharmaceutical Sciences, vol. 66, No. 1, Jan. 1977, pp. 1-20.

Hans Bundgaard, "(C) Mean to Enhance Penetration," Advanced Drug Delivery Reviews, 8, 1992, pp. 1-38.

Aesop Cho, "Recent Advances in Oral Prodrug Discovery," Annual Reports in Medicinal Chemistry, vol. 41, 2006, pp. 395-407.

Sumanta Kumar Pal et al., "Triple-negative breast cancer: Novel therapies and new directions," Maturitas, 63, 2009, pp. 269-274.

Peter G.M. Wuts et al., "Protection for the Hydroxyl Group, Including 1,2- and 1,3-Diols," Greene's Protective Groups in Organic Synthesis, Fourth Edition, 2007, 9 pages.

Peter G.M. Wuts et al., "Protection for the Amino Group," Greene's Protective Groups in Organic Synthesis, Fourth Edition, 2007, 11 pages.

Jean-Christopher Ame, et al., "The PARP suerfamily," Bioessays, 26.8, 2004, pp. 882-893.

M. William Audeh et al., "Oral poly (ADP-ribose) polymerase inhibitor olaparib in patients with BRCA1 or BRCA2 mutations and recurrent ovarian cancer: a proof-of-concept trial," Lancent, vol. 376, Jul. 24, 2010, pp. 245-251.

Helen E. Bryant et al., "Specific killing of BRCA2-deficient tumours with inhibitors of poly(ADP-ribose) polymerase," Nature, vol. 434, Apr. 14, 2005, pp. 913-914.

Ting-Chao Chou, "Theoretical Basis, Experimental Design, and Computerized Simulation of Synergism and Antagonism in Drug Combination Studies," Pharmacol, vol. 58, No. 3, 2006, pp. 621-681.

Francoise Dantzer et al., "Base Excision Repair is Impaired in Mammalian Cells Lacking Poly(ADP-ribose) Polymerase-1," Biochemistry, 39, 2000, pp. 7559-7569.

Hannah Farmer et al., "Targeting the DAN repair defect in BRCA mutant cells as a therapeutic strategy," Nature, vol. 434, Apr. 14, 2005, pp. 917-921.

Shingo Hirai et al., "Metabolites of Febrifugine and Its Synthetic Analogue by Mouse Liver S9 and Their Antimalarial Activity against Plasmodium Malaria Parasite," J. Med. Chem, 46, 2003, pp. 4351-4359.

Prakash Jagtop et al., "Poly(ADP-Ribose) Polymerase and the Therapeautic Effects of Its Inhibitors," National Reviews Drug Discovery, vol. 4, May 2005, pp. 421-440.

W. Lee Kraus et al., "PARP Goes Transcription," Cell, vol. 113, Jun. 13, 2003, 7 pages.

Frederick Leonard et al., "Unnatural Amino Acids. II. Congeners of DL-3-Carboxy-4methexyphenylalanine," J. Med. Chem., 1967, pp. 478-481.

Josiane Menissier De Murcia et al., "Requirement of poly(ADP-ribose) polymerase in recovery from DNA damage in mice and in cells," Proc. Natl. Acad. Sci. USA, vol. 94, Jul. 1997, pp. 7303-7307.

Joyce O'Shaughnessy, M.D., et al., "Iniparib plus Chemotherapy in Metastatic Triple-Negative Breast Cancer," The New England Journal of Medicine, vol. 364, No. 3, Jan. 20, 2011, pp. 205-214.

Ruth Plummer et al., "Phase I Study of the Poly(ADP-Ribose) Polymerase Inhibitor, AG014699, in Combination with Temozolomide in Patients with Advanced Solid Tumors," Clin Cancer Res, 14(23), Dec. 1, 2008, pp. 7917-7923.

Stephen D. Skaper, "Poly(ADP-Ribose) Polymerase-1 in Acute Neuronal Death and Inflammation," Ann. N.Y. Acad. Sci., 993, 2003, pp. 217-228.

Stephen D. Skaper, "Questions and Answers Session VI: Mechanisms of Neuroprotection," Ann. N.Y. Acad. Sci., 993, 2003, pp. 287-288.

Gabor Szabo et al., "Poly(ADP-ribose) polymerase activation in the reperfused myocardium," Cardiovascular, 61, 2004, pp. 471-480.

Andrew Tutt et al., "Oral poly(ADP-ribose) polymerase inhibitor olaparib in patients with BRCA1 or BRCA2 mutations and advanced breast cancer: a proof-of-concept trial," Lancet, vol. 376, Jul. 24, 2010, pp. 235-244.

Richard Wooster, Ph.D. et al., "Breast and Ovarian Cancer," The New England Journal of Medicine, 348(23), Jun. 5, 2003, pp. 2339-2347.

Goto, S. et al., "The Process Development of a Novel Aldose Reductase Inhibitor, FK366, Part 1. Improvement of Discovery Process and New Syntheses of 1-Substituted Quinazolinediones," Organic Process Research & Development 7:700-706, American Chemical Society (2003).

Menear, K.A. et al., "4-[3-(4-Cyclopropanecarbonylpiperazine-1-carbonyl)-4-fluorobenzyl]-2H-phthalazin-1-one: A Novel Bioavailable Inhibitor of Poly(ADP-ribose) Polymerase-1," J. Med. Chem. 51:6581-6591, American Chemical Society (2008).

Office Action for U.S. Appl. No. 14/006,722, § 371(c) Date Sep. 23, 2013, Inventors: Cai et al., U.S. Patent and Trademark Office, Alexandria, VA, mailed May 29, 2014.

English language machine translation of the claims of DE 26 52 144 A1 (document FP2), Oct. 9, 2014.

English language machine translation of the claims of JP 10-195058 A (document FP3), Oct. 9, 2014.

English language machine translation of the claims of JP 2001-302515A (document FP4), Oct. 9, 2014.

English language machine translation of the claims of JP 2002-284699A (document FP5), Oct. 9, 2014.

English language machine translation of the claims of JP 2007-137818A (document FP6), Oct. 9, 2014.

Office Action for U.S. Appl. No. 14/006,722, § 371(c) Date Sep. 23, 2013, Inventors: Cai et al., U.S. Patent and Trademark Office, Alexandria, VA, mailed Dec. 26, 2014.

Office Action for co-pending U.S. Appl. No. 14/006,722; § 371(c) Date Sep. 23, 2013, Inventors: Cai et al., U.S. Patent and Trademark Office, Alexandria, VA, mailed Apr. 3, 2015.

Mitsos, C., "Isosteres in Medicinal Chemistry," 7 pages, Group Meeting, Feb. 1, 2006.

* cited by examiner

QUINAZOLINEDIONES AND THEIR USE

CROSS-REFERENCE TO RELATED APPLICATION AND INCORPORATION BY REFERENCE

The present application is the national phase application of PCT Application No. PCT/US2012/028698, filed Mar. 12, 2012, which claims priority to U.S. Provisional Patent Application No. 61/452,360, filed Mar. 14, 2011, the entirety of both is hereby incorporated by reference.

TECHNICAL FIELD

The present invention relates to quinazolinediones, their preparation and their use in the prevention and treatment of diseases. More specifically, the present invention relates to the use of these compounds to inhibit poly(ADP-ribose) polymerases, commonly known as PARP.

BACKGROUND OF THE INVENTION

Poly(ADP-ribose) polymerases (PARPs) belong to a family of 18 members identified to date, that catalyze the addition of ADP-ribose units to DNA or different acceptor proteins (Ame, J. C., C. Spenlehauer, et al. (2004). Bioessays 26(8): 882-893). PARP-1 is a 113 kDa nuclear protein with three major structural domains: a N-terminal DNA binding domain (DBD) with two zinc fingers, a C-terminal catalytic domain and an auto modification domain. PARP-2 is a nuclear protein shares 68% homology with PARP-1 in its catalytic domain. Among the PARPs, only PARP-1 and PARP-2 are involved in the repair of DNA single strand breaks. PARP-1/2 (PARP-1 and PARP-2) play multiple roles in DNA repair, signal transduction and gene regulation (Kraus, W. L. and J. T. L is (2003). Cell 113(6): 677-683; Ame, J. C., C. Spenlehauer, et al. (2004). Bioessays 26(8): 882-893; Jagtap, P. and C. Szabo (2005). Nat. Rev. Drug Discov. 4(5): 421-440).

PARP-1/2 are recruited to the site of DNA damage and activated upon DNA binding through its zinc fingers, followed by poly (ADP-ribose)ation on histone glutamate residues. This results in a highly negatively charged ADP-ribose chain, which in turn leads to the unwinding and repair of the damaged DNA through the base excision repair mechanism. PARP-1/2 also regulate cell proliferation, differentiation, DNA repair and chromosome stability through interactions with multiple nuclear components such as the nick-sensor DNA ligase III, the adaptor factor XRCC1, DNA polymerase-beta and DNA ligase III, Cockayne syndrome-B protein, Werner syndrome nuclear protein, DNA topoisomerase I activity. PARP-1 is responsible for majority of the DNA damage associated with PARP activity (>90%). Because of its multi-function roles, the activation of PARP-1/2 has been implicated in several human diseases such as cancer, stroke, myocardial infarction, inflammation, hypertension, atherosclerosis and diabetes.

Radiation and chemotherapy are two important therapeutic approaches for cancer treatment. Ionizing radiation and DNA-methylating agents kill cancer cells by mechanisms involving DNA single-strand breaks. However, the single-strand breaks activate PARP-1 and initiate the base excision repair mechanism to repair the damages, which results in reduced potency or drug-resistance. When PARP-1 activity is inhibited, the single strand DNA becomes permanent, which causes genomic dysfunction and apoptosis, eventually cell death (de Murcia, J. M., C. Niedergang, et al. (1997). Proc. Natl. Acad. Sci. U.S.A. 94(14): 7303-7307; Dantzer, F., G. de La Rubia, et al. (2000). Biochemistry 39(25): 7559-7569). Therefore, PARP-1 inhibitor may be used as adjunct anticancer agents to potentiate clinical efficacy of radiation and chemotherapy (de Murcia, J. M., C. Niedergang, et al. (1997). Proc Natl Acad Sci USA 94(14): 7303-7307; Plummer, R., C. Jones, et al. (2008). Clin. Cancer Res. 14(23): 7917-7923).

Breast and ovarian cancers are leading diseases causing death in women. Breast cancer associated gene 1 or 2 (BRCA1 or BRCA2) mutations account for 3-5% of all breast cancers and a greater proportion of ovarian cancers (Wooster, R. and B. L. Weber (2003). N. Engl. J. Med. 348(23): 2339-2347). In "triple negative" breast cancer (deficiency in estrogen receptor a, progesterone receptor expression and HER2 gene), which accounts for approximately 15% of the total breast cancer diagnoses and have a higher likelihood of recurrence and death, the incidence of the mutations are more than 50% (Pal, S. K. and J. Mortimer (2009). Maturitas 63(4): 269-274). BRCA1 and BRCA2 play an integral role in the repair of double-strand breaks in DNA via a mechanism called homologous recombination. BRCA1/2 deficient cells are unable to repair double-strand breaks in DNA, but predominately rely on PARP-1/2 mediated base excision repair to maintain genetic integrity. Inhibition of PARP-1 activity causes synthetic lethality in BRCA1 or 2 mutant cancer cells due to excessive single- and double-strand breaks in DNA, leading to chromosomal aberrations and instability of the genome (Bryant, H. E., N. Schultz, et al. (2005). Nature 434(7035): 913-917; Farmer, H., N. McCabe, et al. (2005). Nature 434(7035): 917-921). Therefore, PARP-1/2 inhibitor may be used as a single agent in treatment of cancers with deficient DNA repair mechanisms (Audeh, M. W., J. Carmichael, et al. (2010). Lancet 376(9737): 245-251; Tutt, A., M. Robson, et al. (2010). Lancet 376(9737): 235-244; O'Shaughnessy, J., C. Osborne, et al. (2011). N. Engl. J. Med. 364(3): 205-214).

PARP-1 activation contributes to various forms of reperfusion injury in brain, heart, kidney, liver and other organs. PARP-1 is excessively activated due to massive damage of DNA and other cellular events under the pathophysiological condition of reperfusion, which leads to rapid consumption of NAD+, depletion of cellular energy, and eventually necrosis. The treatment with PARP inhibitor or PARP1 deficiency reduced infarct size and improved functional outcomes in both brain and heart in preclinical tests (Skaper, S. D. (2003). Ann. N. Y. Acad. Sci. 993: 217-228; discussion 287-288; Szabo, G., L. Liaudet, et al. (2004). Cardiovasc. Res. 61(3): 471-480). PARP-1 inhibitor may be used to treat repufusion diseases such as stroke, and myocardial infarction (Jagtap, P. and C. Szabo (2005). Nat. Rev. Drug Discov. 4(5): 421-440). PARP-1 inhibitors also show pharmacological activity in disease models of inflammation, hypertension, atherosclerosis and diabetic cardiovascular diseases (Jagtap, P. and C. Szabo (2005). Nat. Rev. Drug Discov. 4(5): 421-440).

SUMMARY OF THE INVENTION

In one aspect, compounds are of formula (I), or pharmaceutically acceptable salts, solvates, hydrates, metabolites, or prodrug thereof:

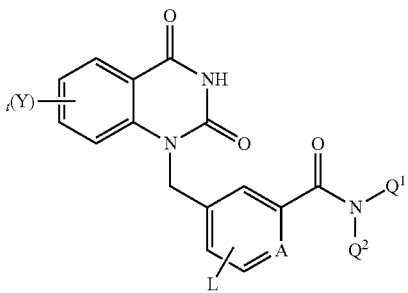

wherein:

A is selected from the group consisting of selected from the group consisting of $CR^a$ and N; where $R^a$ is selected from the group consisting of hydrogen, halogen, and unsubstituted or substituted alkyl;

L is selected from the group consisting of hydrogen, halogen, cyano, nitro, unsubstituted or substituted alkyl, and unsubstituted or substituted alkoxyl;

$Q^1$ and $Q^2$ are independently selected from the group consisting of hydrogen, unsubstituted or substituted alkyl, unsubstituted or substituted alkenyl, unsubstituted or substituted alkynyl, unsubstituted or substituted cycloalkyl, unsubstituted or substituted cycloalkenyl, unsubstituted or substituted heterocycloalkyl, unsubstituted or substituted aryl, and unsubstituted or substituted heteroaryl; or $Q^1$ and $Q^2$ together with the nitrogen atom to which they are attached, may form cyclic moiety selected from the group consisting of unsubstituted or substituted heterocycloalkyl, unsubstituted or substituted heterocycloalkenyl, and unsubstituted or substituted heteroaryl;

each Y is independently selected from the group consisting of hydrogen, halogen, cyano, nitro, unsubstituted or substituted alkyl, $OR^1$, and $NR^1$, $R^2$;

where $R^1$ and $R^2$ are independently selected from the group consisting of hydrogen, unsubstituted or substituted alkyl, unsubstituted or substituted alkenyl, unsubstituted or substituted alkynyl, unsubstituted or substituted cycloalkyl, unsubstituted or substituted cycloalkenyl, and unsubstituted or substituted heterocycloalkyl; and t=0, 1, or 2.

In another aspect, the present disclosure relates to a compound of formula (II), or a pharmaceutically acceptable salt or prodrug thereof:

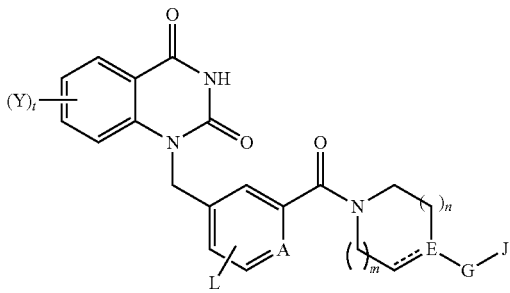

wherein:

A, L, Y and t are as defined in formula (I);
E is N or $CR^3$;
$R^3$ is absent, or $R^3$ is selected from the group consisting of hydrogen, halogen, and unsubstituted or substituted alkyl;
G is absent, or G is selected from the group consisting of unsubstituted or substituted alkyl, O, CO, (CO)O, O(CO)NH, —O—N=, (CO)NH, NH, NH(CO), NH(CO)O, S, $SO_2$, $(SO_2)NH$, and $NH(SO_2)$;
J is absent, or J is selected from the group consisting of hydrogen, halogen, cyano, nitro, hydroxyl, unsubstituted or substituted alkyl, unsubstituted or substituted alkenyl, unsubstituted or substituted alkynyl, unsubstituted or substituted alkoxyl, unsubstituted or substituted cycloalkyl, unsubstituted or substituted cycloalkenyl, unsubstituted or substituted heterocycloalkyl, unsubstituted or substituted aryl, and unsubstituted or substituted heteroaryl;
when E is $CR^3$, $CR^3$, G and J may together form a spiro $C_3$-$C_7$ cycloalkyl or heterocyclic group;
===== denotes a carbon-carbon single or double bond;
m=0, 1, or 2; and
n=0, 1, or 2.

In yet another aspect, the present disclosure relates to a compound of formula (III), or a pharmaceutically acceptable salt or prodrug thereof:

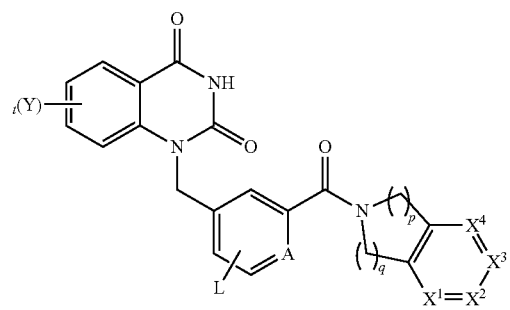

wherein:

A, L, Y and t are as defined in formula (I);
$X^1$, $X^2$, $X^3$ and $X^4$ are each independently selected from the group consisting of N and $CR^4$;
where $R^4$ is selected from the group consisting of hydrogen, halogen, cyano, nitro, unsubstituted or substituted alkyl, unsubstituted or substituted alkenyl, unsubstituted or substituted alkynyl, unsubstituted or substituted cycloalkyl, unsubstituted or substituted cycloalkenyl, unsubstituted or substituted heterocycloalkyl, unsubstituted or substituted aryl, unsubstituted or substituted heteroaryl, $OR^5$, $(CO)R^5$, $(CO)OR^5$, $(CO)NHR^5$, $NHR^5$, $NH(CO)R^5$, $NH(CO)OR^5$, $NH(CO)NHR^5$; $SO_2R^5$, $(SO_2)OR^5$, and $SO_2NHR^5$;
where $R^5$ is selected from the group consisting of hydrogen, unsubstituted or substituted alkyl, unsubstituted or substituted alkenyl, unsubstituted or substituted alkynyl, unsubstituted or substituted cycloalkyl, unsubstituted or substituted cycloalkenyl, unsubstituted or substituted heterocycloalkyl, unsubstituted or substituted aryl, and unsubstituted or substituted heteroaryl;
p=1, or 2; and
q=1, or 2.

In still another aspect, the present disclosure provides methods for the prevention and treatment of diseases associated with PARP activities.

In addition to the compounds provided herein, the present invention provides a composition containing one or more of these compounds.

DETAILED DESCRIPTION OF THE INVENTION

Definitions

Listed below are definitions of various terms used to describe this invention. These definitions apply to the terms as they are used throughout this specification and claims, unless otherwise limited in specific instances, either individually or as part of a larger group.

The term "anti-cancer agent" refers to a compound or drug capable of preventing or inhibiting the advancement of cancer. Examples of such agents include cis-platin, actinomycin D, doxorubicin, vincristine, vinblastine, etoposide, amsacrine, mitoxantrone, tenipaside, taxol, colchicine, cyclosporin A, phenothiazines or thioxantheres.

The term "alkyl" as used herein, refers to saturated, straight- or branched-chain hydrocarbon radicals containing between one and twelve carbon atoms, respectively. Examples of alkyl radicals include, but are not limited to, methyl, ethyl, propyl, isopropyl, n-butyl, tert-butyl, neopentyl, n-hexyl, heptyl, octyl radicals.

The term "alkenyl" as used herein, denotes a monovalent group derived from a hydrocarbon moiety by the removal of a single hydrogen atom wherein the hydrocarbon moiety has at least one carbon-carbon double bond and contains from two to twelve carbon atoms, respectively. Representative alkenyl groups include, but are not limited to, for example, ethenyl, propenyl, butenyl, 1-methyl-2-buten-1-yl, heptenyl, octenyl and the like.

The term "alkynyl" as used herein, denotes a monovalent group derived from a hydrocarbon moiety by the removal of a single hydrogen atom wherein the hydrocarbon moiety has at least one carbon-carbon triple bond and contains from two twelve carbon atoms, respectively. Representative alkynyl groups include, but are not limited to, for example, ethynyl, 1-propynyl, 1-butynyl, heptynyl, octynyl and the like.

The term "alkoxy" as used herein, refers to an oxygen moiety having a further alkyl substituent. Examples of alkoxy include, but not limited to, methoxy, ethoxy, and the like.

The term "aryl," as used herein, refers to a mono, bicyclic or triclyclic carbocyclic ring system having one to three aromatic rings including, but not limited to, phenyl, naphthyl, tetrahydronaphthyl, indanyl, idenyl, anthracenyl and the like.

The term "arylalkyl," as used herein, refers to an aryl group, as defined herein, appended to the parent molecule through an alkyl group, as defined herein. Examples include, but are not limited to, benzyl, phenethyl and the like.

The term "cycloalkyl" as used herein, denotes a monovalent group derived from a monocyclic or polycyclic saturated carbocyclic ring compound by the removal of a single hydrogen atom where the saturated carbocyclic ring compound has from 3 to 12 ring atoms, respectively. Examples of cycloalkyl include, but not limited to, cyclopropyl, cyclobutyl, cyclopentyl, cyclohexyl, bicyclo[2.2.1]heptyl, and bicyclo[2.2.2]octyl.

The term "cycloalkenyl" as used herein, denotes a monovalent group derived from a monocyclic or polycyclic carbocyclic ring compound having at least one carbon-carbon double bond by the removal of a single hydrogen atom where the carbocyclic ring compound has from 3 to 12 ring atoms, respectively. Examples of cycloalkenyl include, but not limited to, cyclopropenyl, cyclobutenyl, cyclopentenyl, cyclohexenyl, cycloheptenyl, cyclooctenyl, and the like.

The term "heteroaryl," as used herein, refers to a mono-, bi-, or tri-cyclic aromatic radical or ring having from five to eighteen ring atoms of which at least one ring atom is selected from S, O and N; wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, triazolyl, tetrazolyl, quinolinyl, isoquinolinyl, benzimidazolyl, benzooxazolyl, quinoxalinyl, and the like.

The term "heteroarylalkyl," as used herein, refers to a heteroaryl group, as defined herein, appended to the parent molecule through an alkyl group, as defined herein. Examples include, but are not limited to, pyridinylmethyl, pyrimidinylethyl and the like.

The term "substituted" as used herein, refers to independent replacement of one, two, or three or more of the hydrogen atoms thereon with substituents including, but not limited to, —F, —Cl, —Br, —I, —OH, protected hydroxy, —$NO_2$, —CN, —$NH_2$, $N_3$, protected amino, alkoxy, thioalkoxy, oxo, -halo-$C_1$-$C_{12}$-alkyl, -halo-$C_2$-$C_{12}$-alkenyl, -halo-$C_2$-$C_{12}$-alkynyl, -halo-$C_3$-$C_{12}$-cycloalkyl, —NH-alkyl, —NH-alkenyl, —NH-alkynyl, —NH-cycloalkyl, —NH-aryl, —NH-heteroaryl, —NH-heterocycloalkyl, -dialkylamino, -diarylamino, -diheteroarylamino, -O-alkyl, -O-alkenyl, —O-alkynyl, —O-cycloalkyl, —O-aryl, —O-heteroaryl, —O-heterocycloalkyl, —C(O)-alkyl, —C(O)-alkenyl, —C(O)-alkynyl, —C(O)-cycloalkyl, —C(O)-aryl, —C(O)-heteroaryl, —C(O)-heterocycloalkyl, —$CONH_2$, —CONH-alkyl, —CONH-alkenyl, —CONH-alkynyl, —CONH-cycloalkyl, —CONH-aryl, —CONH-heteroaryl, —CONH-heterocycloalkyl, —$OCO_2$-alkyl, —$OCO_2$-alkenyl, —$OCO_2$-alkynyl, —$OCO_2$-cycloalkyl, —$OCO_2$-aryl, —$OCO_2$-heteroaryl, —$OCO_2$-heterocycloalkyl, —$OCONH_2$, —OCONH-alkyl, —OCONH-alkenyl, —OCONH-alkynyl, —OCONH-cycloalkyl, —OCONH-aryl, —OCONH-heteroaryl, —CONH-heterocycloalkyl, —NHC(O)-alkyl, —NHC(O)-alkenyl, —NHC(O)-alkynyl, —NHC(O)-cycloalkyl, —NHC(O)-aryl, —NHC(O)-heteroaryl, —NHC(O)-heterocycloalkyl, —$NHCO_2$-alkyl, —$NHCO_2$-alkenyl, —$NHCO_2$-alkynyl, —$NHCO_2$-cycloalkyl, —$NHCO_2$-aryl, —$NHCO_2$-heteroaryl, —$NHCO_2$— heterocycloalkyl, —NHC(O)$NH_2$, —NHC(O)NH-alkyl, —NHC(O)NH-alkenyl, —NHC(O)NH-alkynyl, —NHC(O)NH-cycloalkyl, —NHC(O)NH-aryl, —NHC(O)NH-heteroaryl, —NHC(O)NH-heterocycloalkyl, NHC(S)$NH_2$, —NHC(S)NH-alkyl, —NHC(S)NH-alkenyl, —NHC(S)NH-alkynyl, —NHC(S)NH-cycloalkyl, —NHC(S)NH-aryl, —NHC(S)NH-heteroaryl, —NHC(S)NH-heterocycloalkyl, —NHC(NH)$NH_2$, —NHC(NH)NH-alkyl, —NHC(NH)NH-alkenyl, —NHC(NH)NH-alkynyl, —NHC(NH)NH-cycloalkyl, —NHC(NH)NH-aryl, —NHC(NH)NH-heteroaryl, —NHC(NH)NH-heterocycloalkyl, —NHC(NH)-alkyl, —NHC(NH)-alkenyl, —NHC(NH)-alkynyl, —NHC(NH)-cycloalkyl, —NHC(NH)-aryl, —NHC(NH)-heteroaryl, —NHC(NH)-heterocycloalkyl, —C(NH)NH-alkyl, —C(NH)NH-alkenyl, —C(NH)NH-alkynyl, —C(NH)NH-cycloalkyl, —C(NH)NH-aryl, —C(NH)NH-heteroaryl, —C(NH)NH-heterocycloalkyl, —S(O)-alkyl, —S(O)-alkenyl, —S(O)-alkynyl, —S(O)-cycloalkyl, —S(O)-aryl, —S(O)-heteroaryl, —S(O)-heterocycloalkyl —$SO_2NH_2$, —$SO_2$NH-alkyl, —$SO_2$NH-alkenyl, —$SO_2$NH-alkynyl, —$SO_2$NH-cycloalkyl, —$SO_2$NH-aryl, —$SO_2$NH-heteroaryl, —$SO_2$NH-heterocycloalkyl, —$NHSO_2$-alkyl, —$NHSO_2$-alkenyl, —$NHSO_2$-alkynyl, —$NHSO_2$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, -cycloalkyl, polyalkoxyalkyl, polyalkoxy, -methoxymethoxy, -methoxyethoxy, —SH, —S-alkyl, —S-alkenyl, —S-alkynyl, —S-cycloalkyl, —S-aryl, —S-heteroaryl, —S-heterocycloalkyl, methylthiomethyl, or -L'-R', wherein L' is $C_1$-$C_6$alkylene, $C_2$-$C_6$alkenylene or $C_2$-$C_6$alkynylene, and R' is aryl, heteroaryl, heterocyclic, $C_3$-$C_{12}$cycloalkyl or $C_3$-$C_{12}$cycloalkenyl. It is understood that the aryls, heteroaryls, alkyls, and the like can be further substituted. In some cases, each substituent in a substituted moiety is additionally optionally substituted with one or more groups, each group being independently selected from —F, —Cl, —Br, —I, —OH, —$NO_2$, —CN, or —$NH_2$.

In accordance with the invention, any of the aryls, substituted aryls, heteroaryls and substituted heteroaryls described herein, can be any aromatic group. Aromatic groups can be substituted or unsubstituted.

It is understood that any alkyl, alkenyl, alkynyl, cycloalkyl and cycloalkenyl moiety described herein can also be an aliphatic group, an alicyclic group or a heterocyclic group. An "aliphatic group" is non-aromatic moiety that may contain any combination of carbon atoms, hydrogen atoms, halogen atoms, oxygen, nitrogen or other atoms, and optionally contain one or more units of unsaturation, e.g., double and/or triple bonds. An aliphatic group may be straight chained, branched or cyclic and preferably contains between 1 and 24 carbon atoms, more typically between about 1 and about 12 carbon atoms. In addition to aliphatic hydrocarbon groups, aliphatic groups include, for example, polyalkoxyalkyls, such as polyalkylene glycols, polyamines, and polyimines, for example. Such aliphatic groups may be further substituted. It is understood that aliphatic groups may be used in place of the alkyl, alkenyl, alkynyl, alkylene, alkenylene, and alkynylene groups described herein.

The term "alicyclic," as used herein, denotes a monovalent group derived from a monocyclic or polycyclic saturated carbocyclic ring compound by the removal of a single hydrogen atom. Examples include, but not limited to, cyclopropyl, cyclobutyl, cyclopentyl, cyclohexyl, bicyclo[2.2.1]heptyl, and bicyclo[2.2.2]octyl. Such alicyclic groups may be further substituted.

The term "heterocycloalkyl" and "heterocyclic" can be used interchangeably and refer to a non-aromatic 3-, 4-, 5-, 6- or 7-membered ring or a bi- or tri-cyclic group fused system, where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, (iv) any of the above rings may be fused to a benzene ring, and (v) the remaining ring atoms are carbon atoms which may be optionally oxo-substituted. Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, and tetrahydrofuryl. Such heterocyclic groups may be further substituted to give substituted heterocyclic.

It will be apparent that in various embodiments of the invention, the substituted or unsubstituted alkyl, alkenyl, alkynyl, cycloalkyl, cycloalkenyl, cycloalkynyl, arylalkyl, heteroarylalkyl, and heterocycloalkyl are intended to be monovalent or divalent. Thus, alkylene, alkenylene, and alkynylene, cycloaklylene, cycloalkenylene, cycloalkynylene, arylalkylene, hetoerarylalkylene and heterocycloalkylene groups are to be included in the above definitions, and are applicable to provide the formulas herein with proper valency.

As used herein, the term "pharmaceutically acceptable salt" refers to those salts of the compounds formed by the process of the present invention which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base with a suitable organic acid. Examples of pharmaceutically acceptable salts include, but are not limited to, nontoxic acid addition salts e.g., salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

The term "pharmaceutically acceptable prodrugs" as used herein refers to those prodrugs of the compounds formed by the process of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound, which is convertible in vivo by metabolic means (e.g. by hydrolysis) to afford any compound delineated by the formulae of the instant invention. Various forms of prodrugs are known in the art, for example, as discussed in Bundgaard, et al., Advanced Drug Delivery Reviews, 8, 1-38 (1992); Cho, Aesop, Annual Reports in Medicinal Chemistry, Vol 41, 395-407, (2006). Preferably, the prodrugs are in the forms of esters or amides.

The terms "halo" and "halogen," as used herein, refer to an atom selected from fluorine, chlorine, bromine and iodine.

The term "subject" as used herein refers to a mammal. A subject therefore refers to, for example, dogs, cats, horses, cows, pigs, guinea pigs, and the like. Preferably the subject is a human. When the subject is a human, the subject may be referred to herein as a patient.

The term "hydroxy protecting group," as used herein, refers to a labile chemical moiety which is known in the art to protect a hydroxy group against undesired reactions during synthetic procedures. After said synthetic procedure(s) the hydroxy protecting group as described herein may be selectively removed. Hydroxy protecting groups as known in the are described generally in T. H. Greene and P. G., S. M. Wuts, Protective Groups in Organic Synthesis, 4th edition, John Wiley & Sons, New York (2006). Examples of hydroxy protecting groups include benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl)ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, 1,1-dimethyl-2-propenyl, 3-methyl-3-butenyl, allyl, benzyl, para-methoxybenzyldiphenyl-methyl, triphenylmethyl(trityl), tetrahydrofuryl, methoxymethyl, methylthiomethyl, benzyloxymethyl, 2,2,2-trichloroethoxymethyl, 2-(trimethylsilyl)ethoxymethyl, methanesulfonyl, para-toluenesulfonyl, trimethylsilyl, triethylsilyl, triisopropylsilyl, and the like. Preferred hydroxy protecting groups for the present invention are acetyl (Ac or —C(O)CH$_3$), benzoyl (Bz or —C(O)C$_6$H$_5$), and trimethylsilyl (TMS or —Si(CH$_3$)$_3$).

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the are described generally in T. H. Greene and P. G. M. Wuts, Protective Groups in Organic Synthesis, 4th edition, John Wiley & Sons, New York (2006). Examples of amino protecting groups include, but are not limited to, t-butoxycarbonyl, 9-fluorenylmethoxycarbonyl, benzyloxycarbonyl, and the like.

The term "protected hydroxy," as used herein, refers to a hydroxy group protected with a hydroxy protecting group, as defined above, including benzoyl, acetyl, trimethylsilyl, triethylsilyl, methoxymethyl groups.

The term "acyl" includes residues derived from acids, including but not limited to carboxylic acids, carbamic acids, carbonic acids, sulfonic acids, and phosphorous acids. Examples include aliphatic carbonyls, aromatic carbonyls, aliphatic sulfonyls, aromatic sulfinyls, aliphatic sulfinyls, aromatic phosphates and aliphatic phosphates. Examples of aliphatic carbonyls include, but are not limited to, acetyl, propionyl, 2-fluoroacetyl, butyryl, 2-hydroxy acetyl, and the like.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such solvents are well known to those skilled in the art, and individual solvents or mixtures thereof may be preferred for specific compounds and reaction conditions, depending upon such factors as the solubility of reagents, reactivity of reagents and preferred temperature ranges.

The terms "protogenic organic solvent" or "protic solvent" as used herein, refer to a solvent that tends to provide protons, such as an alcohol, for example, methanol, ethanol, propanol, isopropanol, butanol, t-butanol, and the like. Such solvents are well known to those skilled in the art, and individual solvents or mixtures thereof may be preferred for specific compounds and reaction conditions, depending upon such factors as the solubility of reagents, reactivity of reagents and preferred temperature ranges.

The term "metabolite" refers to the intermediates and products of metabolism.

"Pharmaceutically acceptable" carrier, diluent, or excipient is a carrier, diluent, or excipient compatible with the other ingredients of the formulation and not deleterious to the recipient thereof.

"Therapeutically effective amount" refers to an amount sufficient to effect treatment when administered to a patient in need of treatment.

"Treating" or "treatment" as used herein refers to the treating or treatment of a disease or medical condition (such as a cancer) in a patient, such as a mammal (particularly a human or a companion animal) which includes:

ameliorating the disease or medical condition, i.e., eliminating or causing regression of the disease or medical condition in a patient;

suppressing the disease or medical condition, i.e., slowing or arresting the development of the disease or medical condition in a patient; or alleviating the symptoms of the disease or medical condition in a patient.

The term "composition" as used herein is intended to encompass a product comprising the specified ingredients in the specified amounts, as well as any product which results, directly or indirectly, from combination of the specified ingredients in the specified amounts. By "pharmaceutically-acceptable" it is meant the carrier, diluent or excipient must be compatible with the other ingredients of the formulation and not deleterious to the recipient thereof.

The pharmaceutical compositions for the administration of the compounds of this invention may conveniently be presented in unit dosage form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions and self emulsifications, hard or soft capsules, or syrups or elixirs. Compositions intended for oral use may be prepared according to any method known to the art for the manufacture of pharmaceutical compositions. Such compositions may contain one or more agents selected from sweetening agents, flavoring agents, coloring agents and preserving agents in order to provide pharmaceutically elegant and palatable preparations. Tablets contain the active ingredient in admixture with other non-toxic pharmaceutically acceptable excipients which are suitable for the manufacture of tablets. These excipients may be, for example, inert diluents such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example PVP, cellulose, PEG, starch, gelatin or acacia, and lubricating agents, for example magnesium stearate, stearic acid or talc. The tablets may be uncoated or they may be coated enterically or otherwise by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Additionally, emulsions can be prepared with a non-water miscible ingredient such as oils and stabilized with surfactants such as mono-diglycerides, PEG esters and the like.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinyl-pyrrolidone, gum tragacanth and gum acacia; dispersing or wetting agents may be a naturally occurring phosphatide, for example lecithin, or condensation products of an alkylene oxide with fatty acids, for example, polyoxyethylene stearate, or condensation products of ethylene oxide with long chain aliphatic alcohols, for example, heptadeca-ethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example, ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil in water emulsions. The oily phase may be a vegetable oil, for example olive oil or arachis oil, or a mineral oil, for example liquid paraffin or mixtures of these. Suitable emulsifying agents may be naturally occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents. Oral solutions can be prepared in combination with, for example, cyclodextrin, PEG and surfactants.

The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non toxic parenterally acceptable diluent or solvent, for example as a solution in 1,3-butane diol. Among the acceptable vehicles and solvents that may be employed are water, Ringer's solution and isotonic sodium chloride solution. In addition, sterile, axed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable nonirritating excipient which is solid at ordinary temperatures but liquid at the rectal temperature and will therefore melt in the rectum to release the drug. Such materials are cocoa butter and polyethylene glycols. Additionally, the compounds can be administered via ocular delivery by means of solutions or ointments. Still further, transdermal delivery of the subject compounds can be accomplished by means of iontophoretic patches and the like.

For topical use, creams, ointments, jellies, solutions or suspensions containing the compounds of the present invention are employed. As used herein, topical application is also meant to include the use of mouth washes and gargles.

The pharmaceutical compositions and methods of the present invention may further comprise other therapeutically active compounds as noted herein, such as those applied in the treatment of the above mentioned pathological conditions.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques, which are known to those skilled in the art. When the compounds described herein contain olefinic double bonds or other centers of geometric asymmetry, and unless specified otherwise, it is intended that the compounds include both E and Z geometric isomers. Likewise, all tautomeric forms are also intended to be included. The configuration of any carbon-carbon double bond appearing herein is selected for convenience only and is not intended to designate a particular configuration unless the text so states; thus a carbon-carbon double bond depicted arbitrarily herein as trans may be cis, trans, or a mixture of the two in any proportion.

The synthesized compounds can be separated from a reaction mixture and further purified by a method such as column chromatography, high pressure liquid chromatography, or recrystallization. Additionally, the various synthetic steps may be performed in an alternate sequence or order to give the desired compounds. In addition, the solvents, temperatures, reaction durations, etc. delineated herein are for purposes of illustration only and variation of the reaction conditions can produce the desired products of the present invention.

The compounds of this invention may be modified by appending various functionalities via synthetic means delineated herein to enhance selective biological properties. Such modifications include those which increase biological penetration into a given biological system (e.g., blood, lymphatic system, central nervous system), increase oral availability, increase solubility to allow administration by injection, alter metabolism and alter rate of excretion.

Certain compounds of the present invention can exist in unsolvated forms as well as solvated forms, including hydrated forms. In general, both solvated forms and unsolvated forms are intended to be encompassed within the scope of the present invention.

Certain compounds of the present invention may exist in multiple crystalline or amorphous forms (i.e., as polymorphs). In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers (e.g., separate enantiomers) are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

A compound of formula (I) can be administered alone or in combination with one or more other therapeutic agents, possible combination therapy taking the form of fixed combinations or administration of a compound of the invention and one or more other therapeutic agents being staggered or given independently of one another, or the combined administration of fixed combinations and one or more other therapeutic agents.

ABBREVIATIONS

Abbreviations which have been used in the descriptions of the schemes and the examples that follow are:
aq. for aqueous;
AIBN for 2,2'-Azobis(2-methylpropionitrile)
DBU for 1,8-diazabicyclo[5.4.0]undec-7-ene;
DCM for dichloromethane;
DIAD for diisopropyl azodicarboxylate;
DIEA or DIPEA for diisopropyl ethylamine;
DMAP for N,N-dimethylaminopyridine;
DME for ethylene glycol dimethyl ether;
DMF for N,N-dimethyl formamide;
DMSO for dimethylsulfoxide;
EDCI or EDC for 1-(3-diethylaminopropyl)-3-ethylcarbodiimide hydrochloride;
ESI for electrospray ionization;
Et for ethyl;
EtOAc for ethyl acetate;
g for gram(s);
h for hour(s);
HATU for O-(7-Azabenzotriazole-1-yl)-N,N,N',N'-tetramethyluronium hexafluorophosphate;
HBTU for 2-(1H-benzotriazol-1-yl)-1,1,3,3-tetramethyluronium hexafluorophosphate
HPLC for high-performance liquid chromatography;
Me for methyl;
MeOH for methanol;
mg for milligram(s);
min for minute(s);
MS for mass spectrometry;
NBS for N-Bromosuccinimide
NMR for nuclear magnetic resonance;
Ph for phenyl;
rt for room temperature;
TEA for triethyl amine;
TFA for trifluoroacetic acid;
THF for tetrahydrofuran;
TLC for thin layer chromatography;
PPh$_3$ for triphenylphosphine;
tBOC or Boc for tert-butyloxy carbonyl;

The identification of small-molecules that specifically modulate PARP activity, particularly PARP-1 and PARP-2, serves therapeutic approaches for treatment of cancers, inflammation, cardiovascular, metabolic and neurological disorders.

In the first embodiment, the present invention is a compound of formula (I), or a pharmaceutically acceptable salt or prodrug thereof:

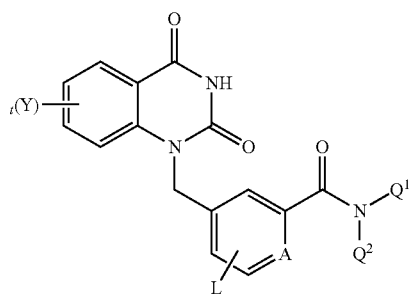

wherein:
A is selected from the group consisting of selected from the group consisting of CR$^a$ and N; where R$^a$ is selected from the group consisting of hydrogen, halogen, and unsubstituted or substituted alkyl;
L is selected from the group consisting of hydrogen, halogen, cyano, nitro, unsubstituted or substituted alkyl, and unsubstituted or substituted alkoxyl;
Q$^1$ and Q$^2$ are independently selected from the group consisting of hydrogen, unsubstituted or substituted alkyl, unsubstituted or substituted alkenyl, unsubstituted or substituted alkynyl, unsubstituted or substituted cycloalkyl, unsubstituted or substituted cycloalkenyl, unsubstituted or substituted heterocycloalkyl, unsubstituted or substituted aryl, and unsubstituted or substituted heteroaryl; or $Q^1$ and $Q^2$ together with the nitrogen atom to which they are attached, may form cyclic moiety selected from the group consisting of unsubstituted or substituted heterocycloalkyl, unsubstituted or substituted heterocycloalkenyl, and unsubstituted or substituted heteroaryl;

each Y is independently selected from the group consisting of hydrogen, halogen, cyano, nitro, unsubstituted or substituted alkyl, $OR^1$, and $NR^1$, $R^2$;

where $R^1$ and $R^2$ are independently selected from the group consisting of hydrogen, unsubstituted or substituted alkyl, unsubstituted or substituted alkenyl, unsubstituted or substituted alkynyl, unsubstituted or substituted cycloalkyl, unsubstituted or substituted cycloalkenyl, and unsubstituted or substituted heterocycloalkyl; and t=0, 1, or 2.

Preferably, A is selected from the group consisting of CH, N, CF and CCl. Preferably, Y is hydrogen. Preferably, L is hydrogen.

In another embodiment, the present invention relates to a compound of formula (II), or a pharmaceutically acceptable salt or prodrug thereof:

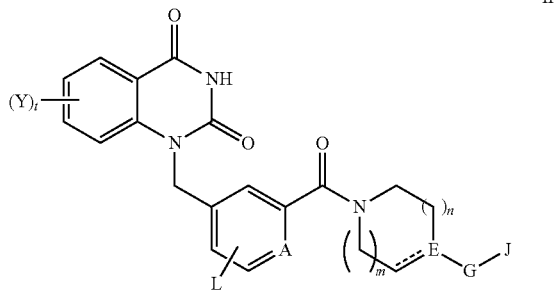

II wherein:
A, L, Y and t are as defined in formula (I);
E is N or $CR^3$;
$R^3$ is absent, or $R^3$ is selected from the group consisting of hydrogen, halogen, and unsubstituted or substituted alkyl;
G is absent, or G is selected from the group consisting of unsubstituted or substituted alkyl, O, CO, (CO)O, O(CO)NH, —O—N=, (CO)NH, NH, NH(CO), NH(CO)O, S, $SO_2$, $(SO_2)NH$, and $NH(SO_2)$);
J is absent, or J is selected from the group consisting of hydrogen, halogen, cyano, nitro, hydroxyl, unsubstituted or substituted alkyl, unsubstituted or substituted alkenyl, unsubstituted or substituted alkynyl, unsubstituted or substituted alkoxyl, unsubstituted or substituted cycloalkyl, unsubstituted or substituted cycloalkenyl, unsubstituted or substituted heterocycloalkyl, unsubstituted or substituted aryl, and unsubstituted or substituted heteroaryl;
═══ denotes a carbon-carbon single or double bond;
m=0, 1, or 2; and
n=0, 1, or 2.

In one preferred embodiment, E is $CR^3$. $CR^3$, G and J may form a spiro $C_3$-$C_7$ cycloalkyl or heterocyclic group.

In one embodiment, Y is hydrogen. In another embodiment, L is hydrogen. In some embodiments, E is N or CH.

Preferably, A is selected from the group consisting of CH, N, CF and CCl.

In one embodiment, G is absent. In one embodiment, G is selected from the group consisting of O, C(O), C(O)O, C(O)NH, O(CO)NH, and —O—N=.

In one embodiment, m is 0 or 1. In one embodiment, n is 0 or 1.

In one embodiment, J is selected from the group consisting of hydrogen, halogen, hydroxyl, unsubstituted or substituted $C_{3-6}$ cycloalkyl, unsubstituted or substituted $C_{1-4}$ alkoxyl, unsubstituted or substituted $C_{1-4}$ alkyl, unsubstituted or substituted phenyl, unsubstituted or substituted pyridinyl, unsubstituted or substituted pyrrolidinyl, unsubstituted or substituted piperazinyl, unsubstituted or substituted pyrazole, unsubstituted or substituted imidazole, unsubstituted or substituted indoline, unsubstituted or substituted pyrimidinyl, unsubstituted or substituted oxazole, unsubstituted or substituted isoxazole, unsubstituted or substituted pyrazinyl, and unsubstituted or substituted tetrahydrofuran. Preferably, J is selected from the group consisting of hydrogen, cyclopropyl, cyclopentyl, ethyl, isopropyl, tert-butyl, fluoro, methoxyl, hydroxyl, and difluoromethyl.

In another embodiment, the present invention relates to a compound of formula (III), or a pharmaceutically acceptable salt or prodrug thereof:

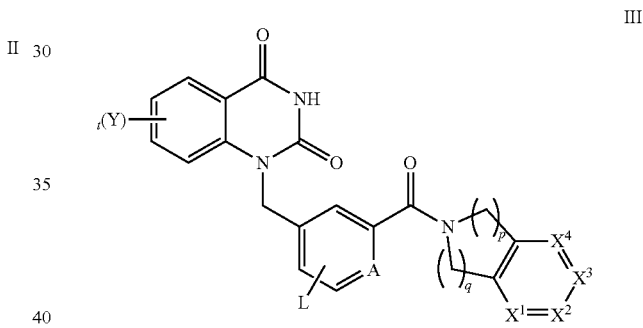

III wherein:
A, L, Y and t are as defined in formula (I);
$X^1$, $X^2$, $X^3$ and $X^4$ are each independently selected from the group consisting N and $CR^4$;

where $R^4$ is selected from the group consisting of hydrogen, halogen, cyano, nitro, unsubstituted or substituted alkyl, unsubstituted or substituted alkenyl, unsubstituted or substituted alkynyl, unsubstituted or substituted cycloalkyl, unsubstituted or substituted cycloalkenyl, unsubstituted or substituted heterocycloalkyl, unsubstituted or substituted aryl, unsubstituted or substituted heteroaryl, $OR^5$, $(CO)R^5$, $(CO)OR^5$, $(CO)NHR^5$, $NHR^5$, $NH(CO)R^5$, $NH(CO)OR^5$, $NH(CO)NHR^5$; $SO_2R^5$, $(SO_2)OR^5$, and $SO_2NHR^5$;

where $R^5$ is selected from the group consisting of hydrogen, unsubstituted or substituted alkyl, unsubstituted or substituted alkenyl, unsubstituted or substituted alkynyl, unsubstituted or substituted cycloalkyl, unsubstituted or substituted cycloalkenyl, unsubstituted or substituted heterocycloalkyl, unsubstituted or substituted aryl, and unsubstituted or substituted heteroaryl;

p=1, or 2; and
q=1, or 2.

In one embodiment, p=1. In another embodiment, q=1.

In one embodiment, Y is hydrogen. In another embodiment, L is hydrogen.

In one embodiment, $X^1$ is N. In another embodiment, $X^1$ and $X^4$ are N. In one embodiment, $X^1$, $X^2$, $X^3$ and $X^4$ are $CR^4$. Preferably, $R^4$ is hydrogen or halogen.

In one embodiment, the present invention relates to a compound of formula (IV), or a pharmaceutically acceptable salt or prodrug thereof:

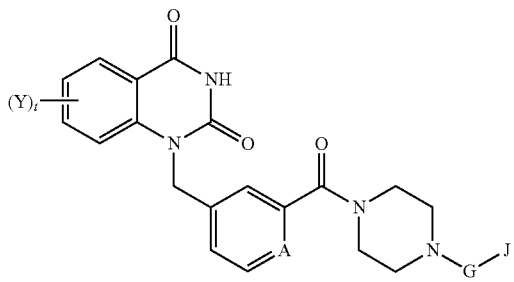

IV wherein G, A, J, Y and t are as defined in formulae (I) and (II).

In one embodiment, G is absent. In another embodiment, G is selected from the group consisting of unsubstituted or substituted alkyl, CO, (CO)O, (CO)NH, and $SO_2$.

In one embodiment, the present invention relates to a compound of formula (V) or a pharmaceutically acceptable salt or prodrug thereof:

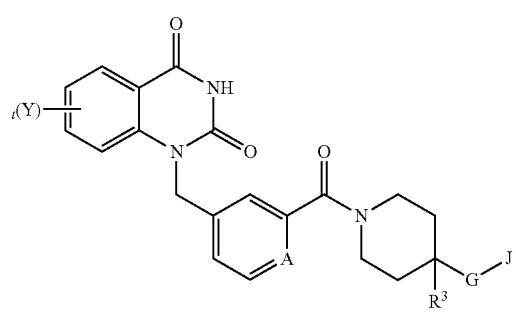

V wherein G, A, $R^3$, J, Y and t are as defined in formulae (I) and (II).

In one embodiment, G is absent. In another embodiment, G is selected from the group consisting of unsubstituted or substituted alkyl, 0, (CO), (CO)O, (CO)NH, —O—N=, NH, NH(CO), NH(CO)NH, S, $SO_2$, $(SO_2)NH$, and $NH(SO_2)$. In one preferred embodiment, the present invention relates to a compound of formula (VI), or a pharmaceutically acceptable salt or prodrug thereof:

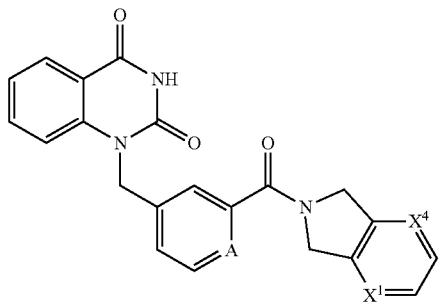

VI wherein A, $X^1$, and $X^4$ are as defined in formula (III).

In one embodiment, A is $CR^a$. Preferably, $R^a$ is fluoro. In one embodiment, $X^1$ and $X^4$ are CH. In another embodiment, $X^1$ and $X^4$ are N. In one embodiment, one of $X^1$ and $X^4$ is N. In one embodiment, one of $X^1$ and $X^4$ is CF.

In another preferred embodiment, the present invention relates to a compound of formula (VII), or a pharmaceutically acceptable salt or prodrug thereof:

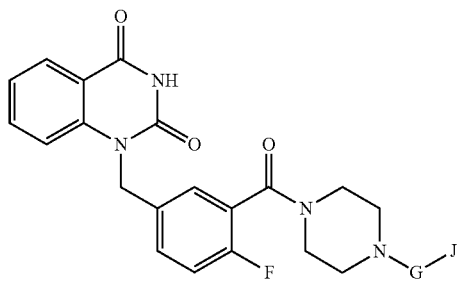

VII wherein G is absent or (CO); and J is selected from the group consisting of unsubstituted or substituted alkyl, unsubstituted or substituted cycloalkyl, unsubstituted or substituted heterocycloalkyl, unsubstituted or substituted aryl, and unsubstituted or substituted heteroaryl.

In one embodiment, G is absent. In one embodiment, G is C(O).

In one embodiment, J is selected from the group consisting of: unsubstituted or substituted phenyl, unsubstituted or substituted pyridinyl, unsubstituted or substituted pyrrolidinyl, unsubstituted or substituted piperazinyl, unsubstituted or substituted pyrazole, unsubstituted or substituted imidazole, unsubstituted or substituted indoline, unsubstituted or substituted pyrimidinyl, unsubstituted or substituted oxazole, unsubstituted or substituted isoxazole, and unsubstituted or substituted pyrazinyl.

In one embodiment, J is selected from the group consisting of:

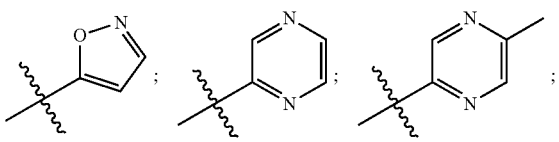

19

-continued

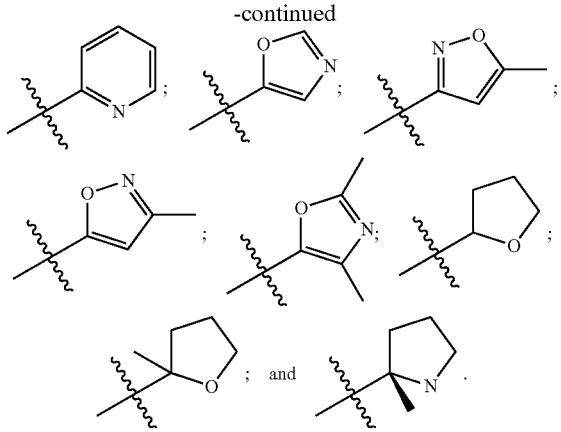

In one preferred embodiment, the present invention relates to a compound of formula (VIII), or a pharmaceutically acceptable salt or prodrug thereof:

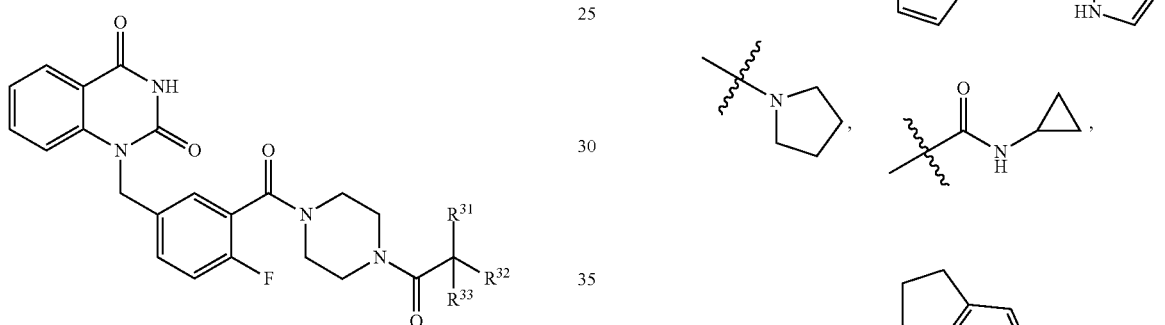

VIII wherein $R^{31}$, $R^{32}$ and $R^{33}$ are each independently selected from the group consisting of hydrogen, halogen, and unsubstituted or substituted alkyl; or $R^{31}$ and $R^{32}$, together with the carbon atom to which they are attached, may form cyclic moiety selected from the group consisting of unsubstituted or substituted cycloalkyl, and unsubstituted or substituted heterocycloalkyl.

In one embodiment, $R^{31}$ and $R^{32}$, together with the carbon atom to which they are attached, form cyclopropyl. In one embodiment, $R^{31}$ and $R^{32}$, together with the carbon atom to which they are attached, form heterocycloalkyl.

In another preferred embodiment, the present invention relates to a compound of formula (IX), or a pharmaceutically acceptable salt or prodrug thereof:

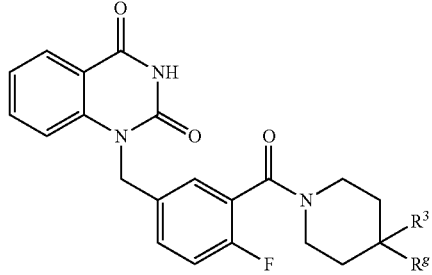

IX

20 wherein $R^3$ is hydrogen or halogen; and wherein $R^9$ is selected from the group consisting of hydrogen, halogen, hydroxyl, unsubstituted or substituted alkoxyl, unsubstituted or substituted cycloalkyl, unsubstituted or substituted heterocycloalkyl, unsubstituted or substituted aryl, and unsubstituted or substituted heteroaryl.

In one embodiment, $R^9$ is selected from the group consisting of hydrogen, F, —OH, hydroxyl, —OEt, —OiPr, —OtBu, —OCHF$_2$,

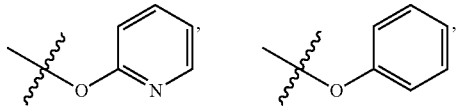

—C(O)OMe, —C(O)OH, and —OC(O)NHEt.

In one preferred embodiment, the present invention relates to a compound of formula (X), or a pharmaceutically acceptable salt or prodrug thereof:

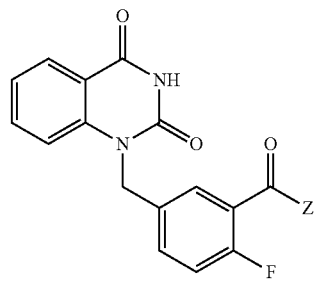

X wherein z is selected from the group consisting of unsubstituted or substituted heterocycloalkyl, and unsubstituted or substituted heteroaryl.

In one embodiment, z is selected from the group consisting of

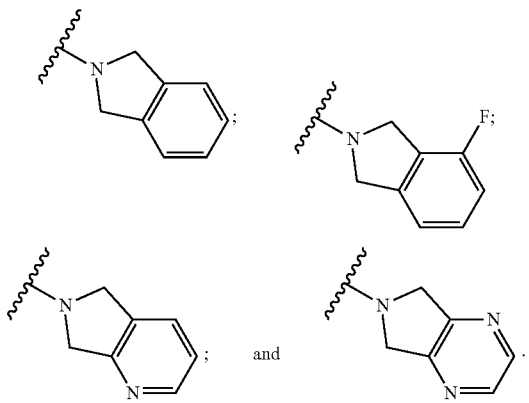

In another preferred embodiment, the present invention relates to a compound of formula (XI), or a pharmaceutically acceptable salt or prodrug thereof:

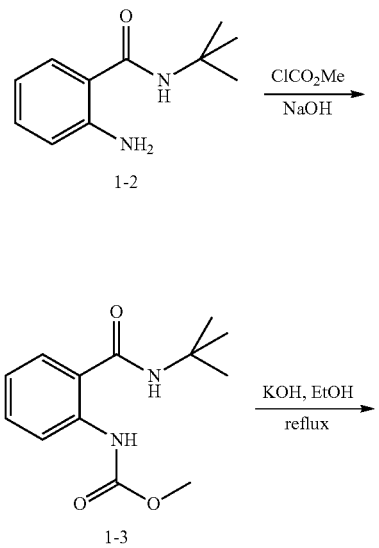

wherein J is selected from the group consisting of unsubstituted or substituted cycloalkyl, unsubstituted or substituted heterocycloalkyl, unsubstituted or substituted aryl, and unsubstituted or substituted heteroaryl.

Synthetic Methods

The compounds and processes of the present invention will be better understood in connection with the following synthetic schemes that illustrate the methods by which the compounds of the invention may be prepared. Other reaction schemes could be readily devised by those skilled in the art.

Scheme 1

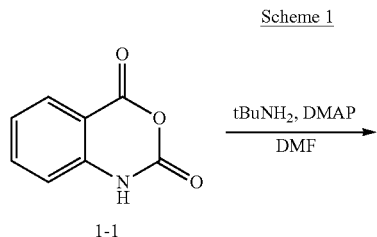

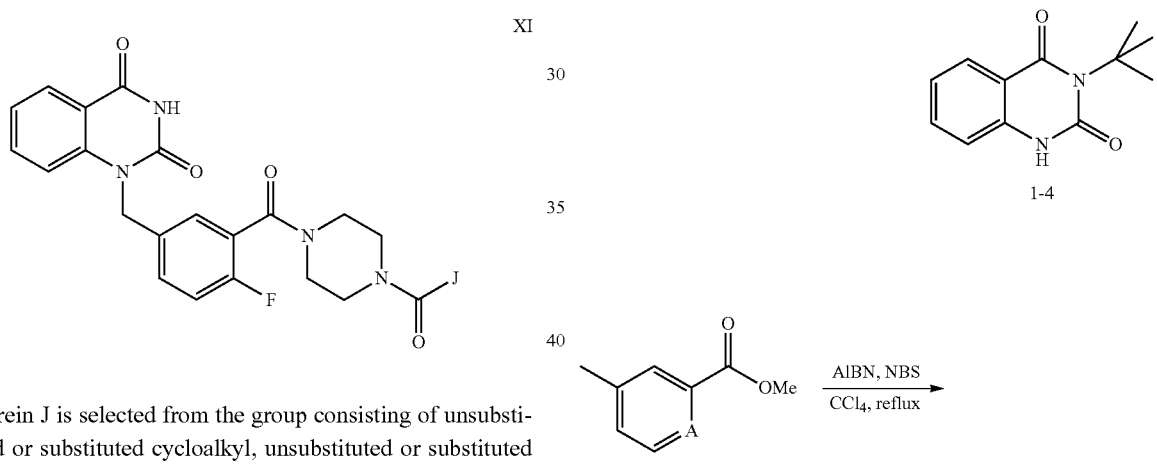

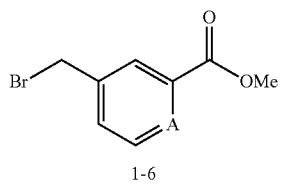

Quinazolinedione 1-4 was prepared according to the procedure reported by Horai, S. etc. in *J. Med. Chem.* 2003, pp 4351. Bromide 1-6 was prepared from the corresponding methyl benzoate by NBS bromination. Quinazolinedione and bromide with substitutes on benzene ring can be prepared with similar methods.

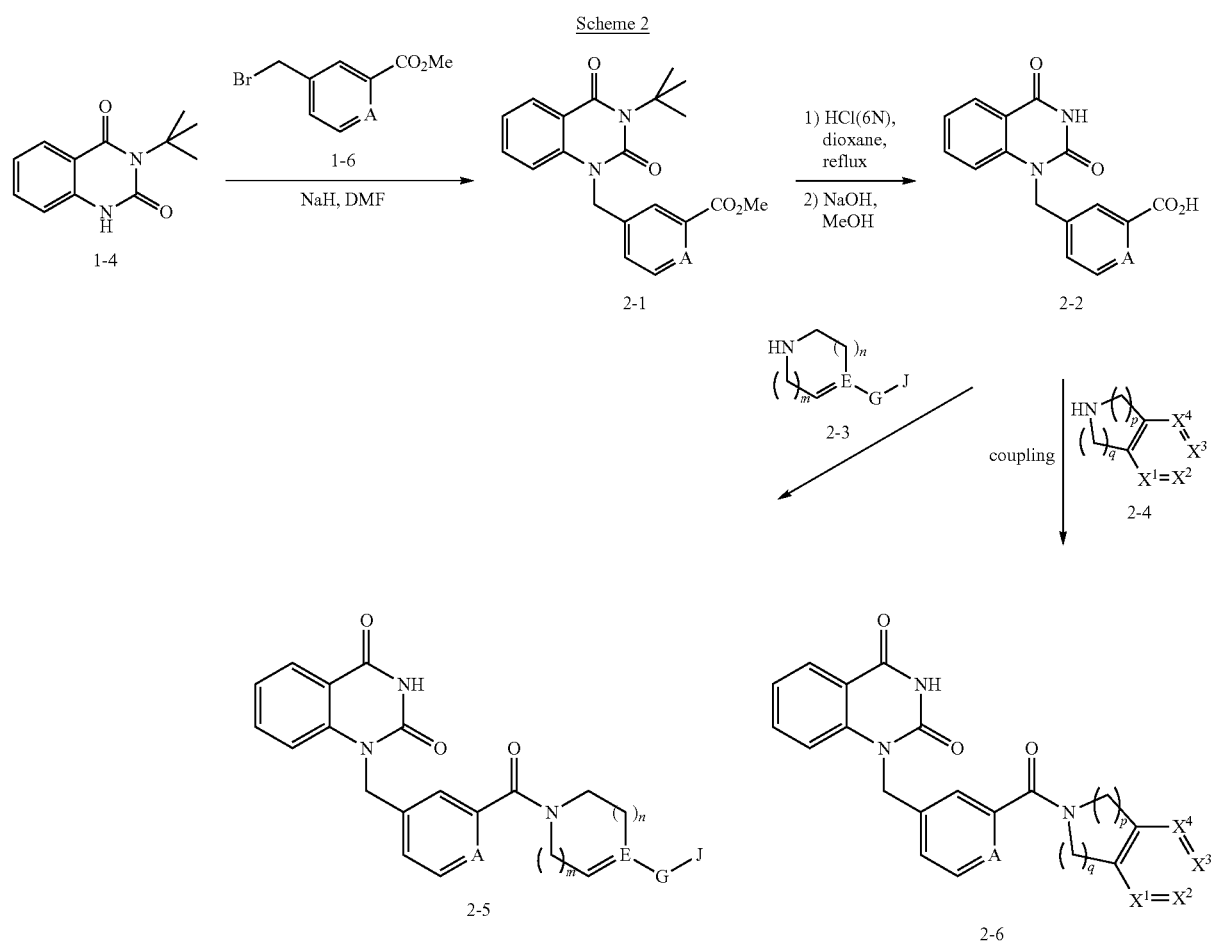
Quinazolinedione 1-4 was deprotonated by NaH, followed by alkylation with bromide 1-6 to afford 2-1. Acidic deprotection followed by basic hydrolysis gave acid 2-2 as a versatile intermediate. Standard amide coupling with corresponding amine can afford final compounds 2-5 or 2-6.
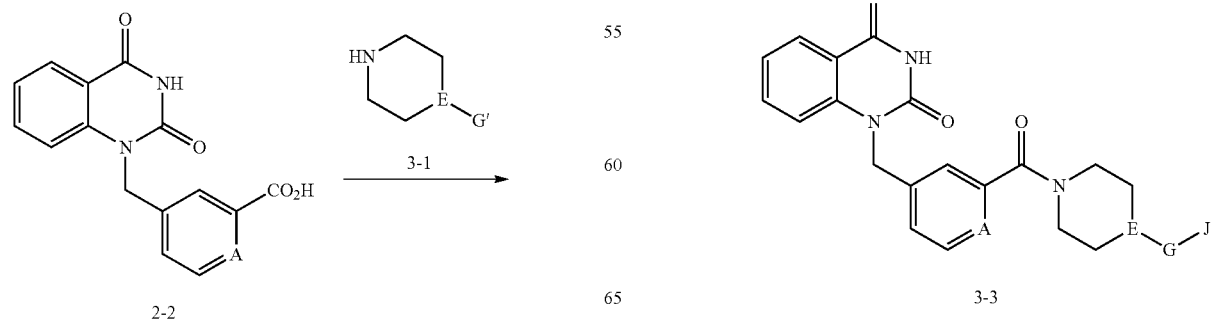
-continued
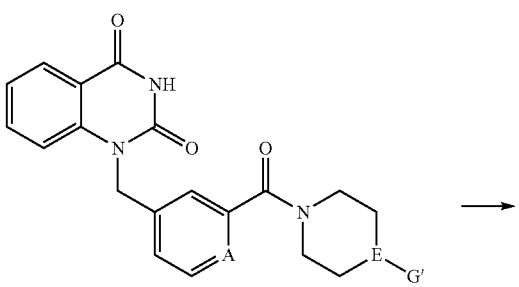

Alternatively, acid 2-2 can couple with a simple amine 3-1 with an easy connecting part G'. Compound 3-2 would serve as common precursors which can be easily elongated with group J. This process will be better understood with two detailed routes illustrated in Scheme 4. Acid 2-2 was treated with 1-boc-piperazine under standard amide coupling conditions, following HCl deprotection gave amine 4-1 as a common intermediate which can further reacted with various acids or chloroformates to give amides 4-2 or carbamates 4-3. Similarly, acid 2-2 reacted with 4-hydroxypiperidine to give alcohol 4-4, which can be subjected to isocynates to afford carbamates 4-5.

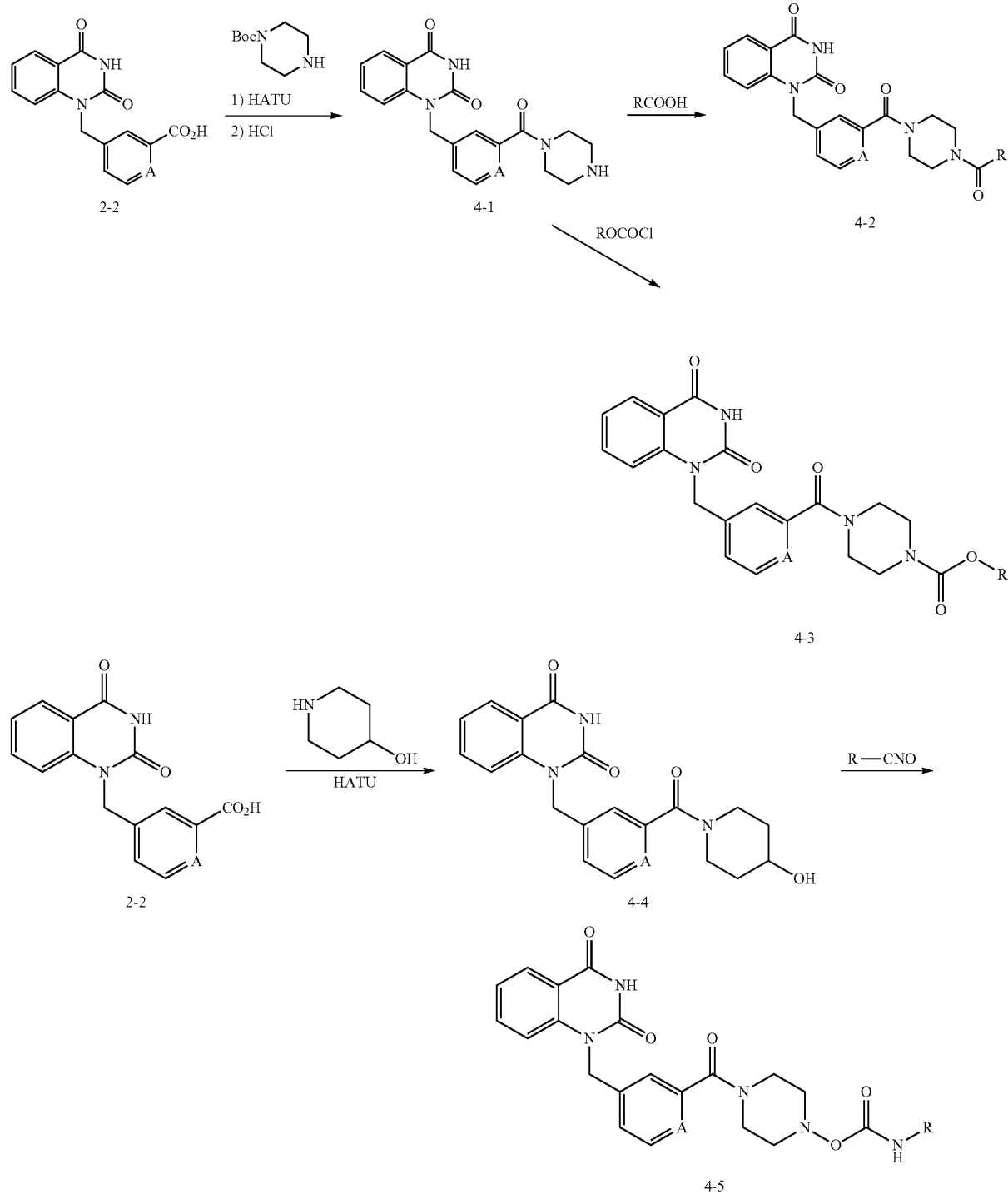

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, relating to the chemical structures, substituents, derivatives, formulations and/or methods of the invention may be made without departing from the spirit of the invention and the scope of the appended claims.

Example 1

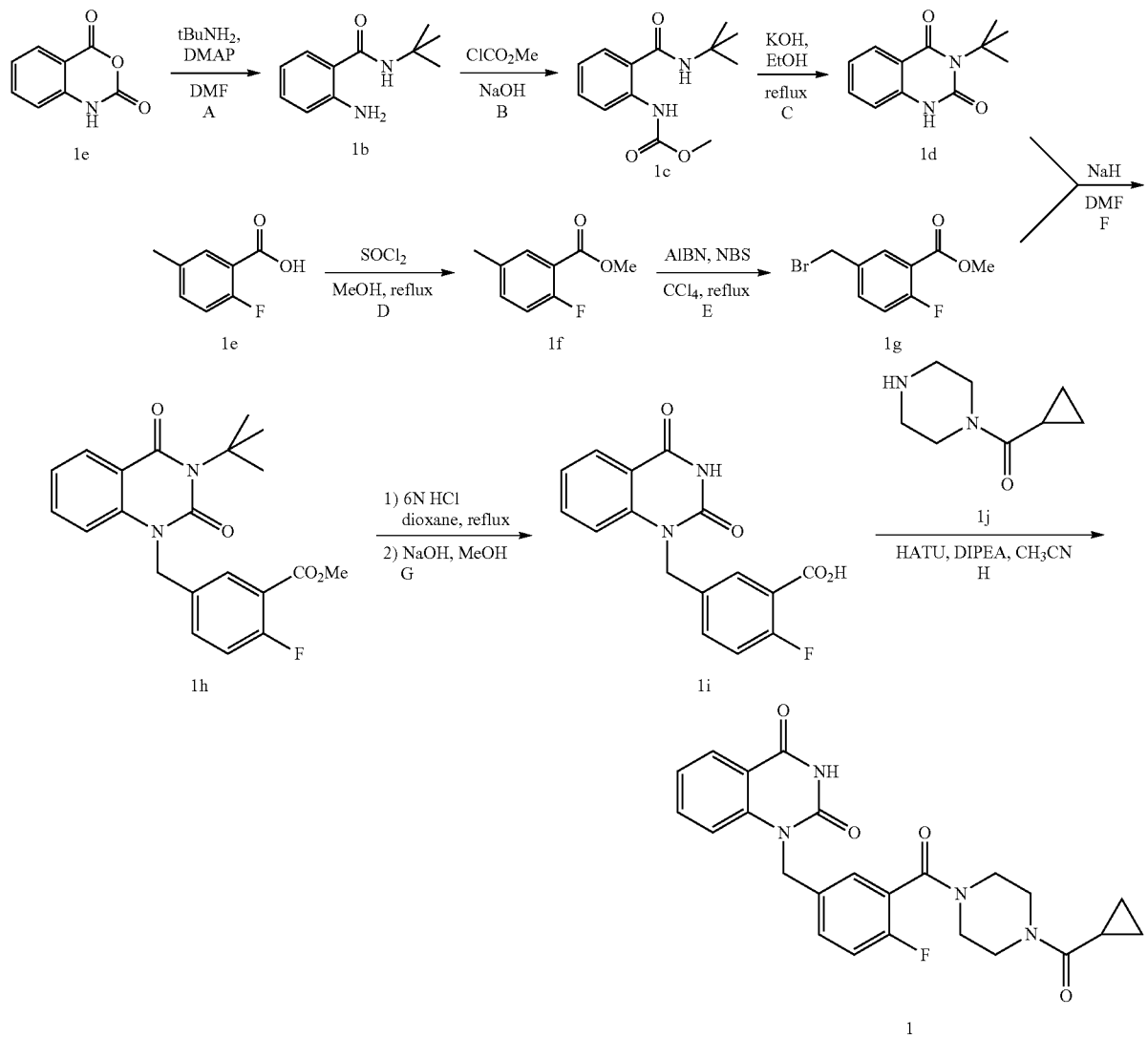

Step 1A

To a solution of isatoic anhydride 1a (12.25 g, 75 mmol) in DMF (75 mL) were added DMAP (915 mg, 7.5 mmol) and tBuNH$_2$ (8.7 mL, 82.6 mmol). The reaction mixture was stirred at room temperature for 4.5 h. Water (150 mL) was added to the mixture. The resulting suspension was filtered. The solid was washed with water and small amount of MeOH, and dried to give light brown solid 1b (5.8 g, 40% yield).

Step 1B

To a solution of 1b (5.8 g, 30.2 mmol) in dioxane (32 mL) in ice bath were added NaOH (1 M, 44 mL) and methyl chloroformate (3.68 mL, 44 mmol). The mixture was stirred for 5 h at room temperature, then HCl (1 M, 70 mL) was added. The precipitate was filtered, washed with water and small amount of MeOH, and dried to give off-white solid 1c (6.9 g, 91% yield).

Step 1C

A mixture of 1c (6.8 g) and KOH (12.2 g) in EtOH (100 mL) was refluxed for 16 h. The mixture was cooled to room temperature and acidified to pH 3~4 by 2M HCl. The resulting suspension was filtered. The solid was washed with water and small amount of MeOH, and dried to give beige solid 1d (3.69 g, 62% yield).

Step 1D

SOCl$_2$ (1 mL) was added dropwise to acid 1e (11 g) in MeOH (60 mL). The solution was refluxed for 20 h. MeOH was removed on rotovapor, and the residue was dissolved in ether. The organic layer was washed with water, saturated NaHCO₃, brine, dried over Na₂SO₄, filtered and concentrated to afford clear oil 1f (10.6 g, 88% yield).

Step 1E

A mixture of 1f (4.67 g, 27.8 mmol), NBS (5.22 g, 29.2 mmol) and AIBN (2.73 g, 16.7 mmol) in CCl₄ (280 mL) was refluxed under N₂ for 6.5 h. The solvents were removed and the residue was suspended with ether. The solid was filtered off. The filtrate was concentrated and purified by silica gel chromatography to give desired product 1 g (3.8 g, 55% yield).

Step 1F

To a solution of 1d (2.9 g, 13.3 mmol) in DMF (40 mL) in ice bath was added 60 wt % NaH (585 mg, 14.6 mmol). The solution was stirred for 30 min and bromide 1 g (3.5 g, 14.2 mmol) was added. The mixture was allowed to warm to room temperature and stirred for 3 h. Saturated NH₄Cl solution was added to quench the reaction. The reaction mixture was extracted with EtOAc. The organic extracts were washed with brine, dried over Na₂SO₄, filtered and concentrated. The residue was purified by silica gel chromatography to give desired product 1 h (4.68 g, 92% yield).

Step 1G

A solution of 1 h (4.65 g) and 6 M HCl (20 mL) in dioxane (27 mL) was refluxed overnight. The resulting suspension was cooled to room temperature and NaOH solution was added to adjust to pH>13. The solution was stirred for 3 h at room temperature. LC-MS showed the complete conversion of 1 h to acid 1i. The solution was acidified to pH<2 by 6 M HCl. The precipitate was filtered, washed with water and small amount of MeOH, and dried to give white solid 1i (3.7 g, 99% yield).

Step 1H

To a solution of 1i (28 mg, 0.089 mmol) in acetonitrile (2 mL) were added DIPEA (48 µL, 0.267 mmol), 1j (15 µL, 0.107 mmol) and HATU (41 mg, 0.107 mmol). The resulting mixture was stirred at room temperature for 2 h and purified by reversed phase prep HPLC to give title compound 1 as white solid (36 mg, 90% yield). The mass of the compound was obtained by Shimadzu LCMS-2020, MS (ESI): m/z=451 [M+H].

Example 2

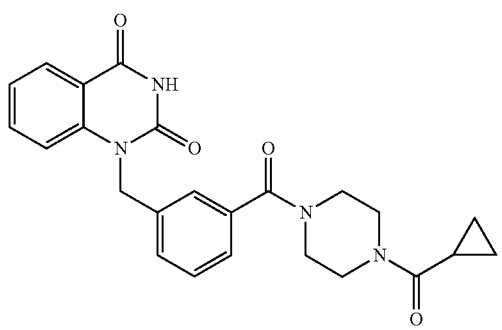

The title compound was made from compound 1d and methyl 3-(bromomethyl)benzoate following procedures described in steps 1F, 1G and 1H in example 1. MS (ESI): m/z=433 [M+H].

Example 3

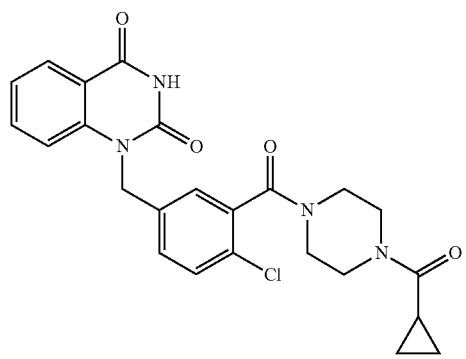

The title compound was made from compound 1d and methyl 5-(bromomethyl)-2-chlorobenzoate (the compound was prepared following procedures described in *J. Med. Chem.* 1967, pp 478 Leonard, F. et al.) following procedures described in steps 1F, 1G and 1H in example 1. MS (ESI): m/z=467 [M+H].

Examples 4 to 18 (Formula IX) were made from acid 1i and the corresponding amine via the similar conditions described in step 1H of Example 1.

TABLE 1

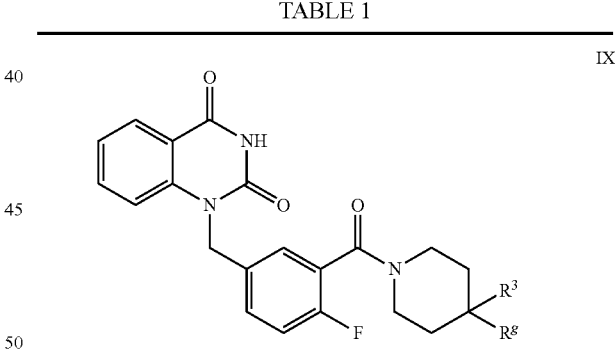

IX

| Example | R³ | Rᵍ | MS(ESI), m/z (M + H) |
|---|---|---|---|
| 4 | H | H | 382 |
| 5 | H | F | 400 |
| 6 | F | F | 418 |
| 7 | H | OH | 398 |
| 8 | H | —OEt | 426 |
| 9 | H | —OiPr | 440 |
| 10 | H | —OtBu | 454 |
| 11 | H | —OCHF₂ | 448 |
| 12 | H | 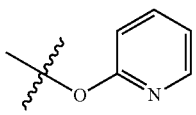 [SMILES: *Oc1ccccn1] | 475 |

TABLE 1-continued

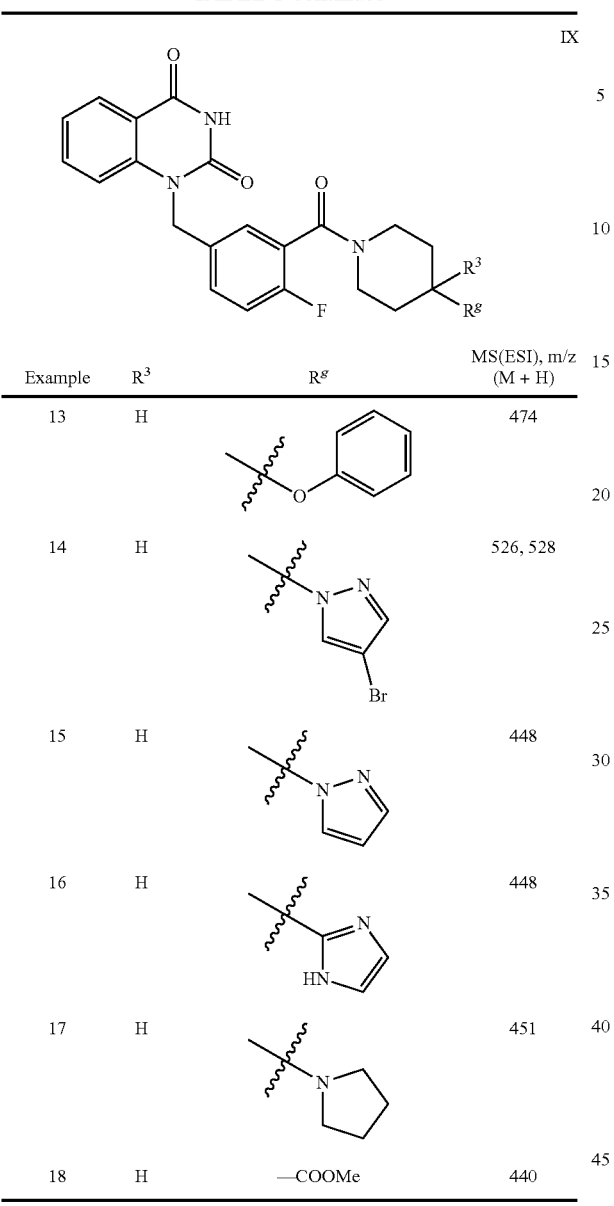

| Example | R³ | R^g | MS(ESI), m/z (M + H) |
|---|---|---|---|
| 13 | H | (phenoxy-dimethyl) | 474 |
| 14 | H | (4-bromopyrazol-1-yl-dimethyl) | 526, 528 |
| 15 | H | (pyrazol-1-yl-dimethyl) | 448 |
| 16 | H | (imidazol-2-yl-dimethyl) | 448 |
| 17 | H | (pyrrolidin-1-yl-dimethyl) | 451 |
| 18 | H | —COOMe | 440 |

Example 19

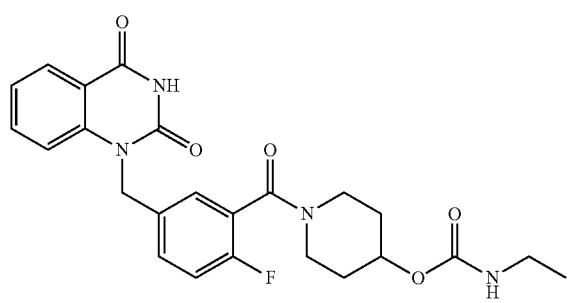

Ethyl isocyanate (13 μL) was added to the title compound of example 7 (7.3 mg) in pyridine (0.8 mL). The mixture was stirred at 50° C. for 2 days and purified by reversed phase prep HPLC to give title compound 19 (8.2 mg). MS (ESI): m/z=469 [M+H].

Example 20

20

(structure of compound 20)

NaOH (0.4 mL, 2M) was added to a solution of the title compound of example 18 (9.7 mg) in MeOH (0.8 mL). The mixture was stirred at room temperature for 2 h and acidified by 4M HCl. The resulting mixture was purified by reversed phase preparative HPLC to give title compound 20 (8.0 mg). MS (ESI): m/z=426 [M+H].

Example 21

21

(structure of compound 21)

The title compound was prepared from compound 20 and cyclopropyl amine via the similar conditions described in step 1H of Example 1. MS (ESI): m/z=465 [M+H].

Example 22

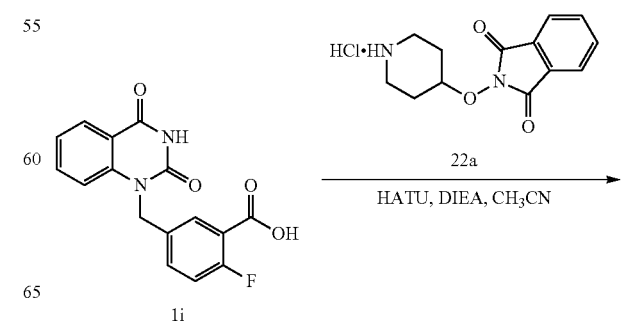

33
-continued

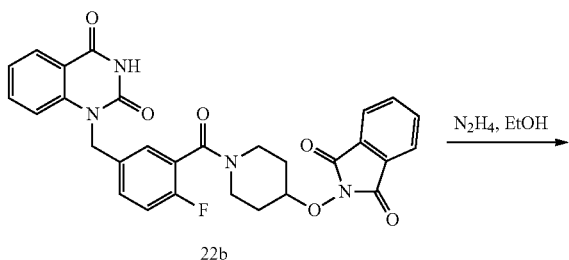

22b

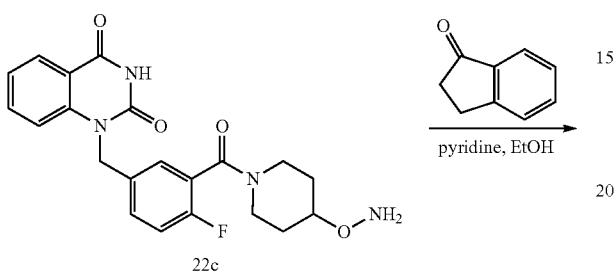

22c

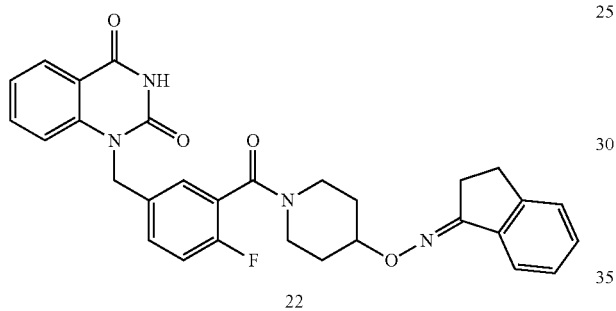

22

Step 22A

To a solution of 1i (37 mg) and 22a (42 mg, the compound was prepared following procedures described in WO2008/150470 A1 TSUNO, N etc) in CH$_3$CN (2 mL) were added DIPEA (65 μL) and HATU (56 mg). The mixture was stirred at room temperature for 2 h. The resulting suspension was filtered and washed with water and MeOH to give white solid 22b. MS (ESI): m/z=543 [M+H].

Step 22B

Hydrazine monohydrate (4 μL) was added a suspension of 22b (20 mg) in EtOH (0.8 mL). The mixture was stirred at room temperature for 45 min and filtered off the solid. The filtrate was purified by reversed phase prep HPLC to give 22c.

Step 22C

To a solution of 22c (3.8 mg) in EtOH (0.8 mL) were added pyridine (50 μL) and 1-indanone (10 mg). The mixture was stirred at room temperature for 18 h and purified by reversed phase preparative HPLC to give title compound 22. MS (ESI): m/z=527 [M+H].

Examples 23 to 29 (Formula X) were made from acid 1i and corresponding amine via the similar conditions described in step 1H of Example 1.

34

TABLE 2

X

| Example | Z | MS(ESI) m/z (M + H) |
|---------|---|----------------------|
| 23 | isoindoline | 416 |
| 24 | 4-fluoroisoindoline | 434 |
| 25 | pyrrolo[3,4-b]pyridine | 417 |
| 26 | pyrrolo[3,4-b]pyrazine | 418 |
| 27 | 4-(pyridin-2-yl)piperazine | 460 |
| 28 | 4-(pyrimidin-2-yl)piperazine | 461 |

TABLE 2-continued

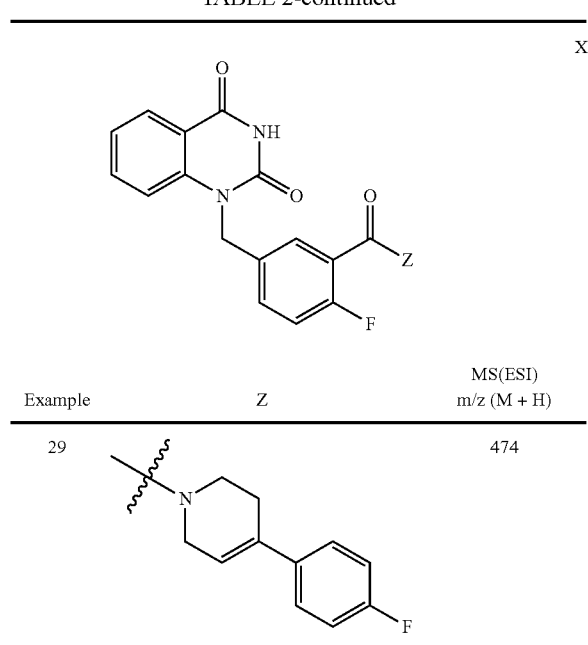

| Example | Z | MS(ESI) m/z (M + H) |
|---|---|---|
| 29 | 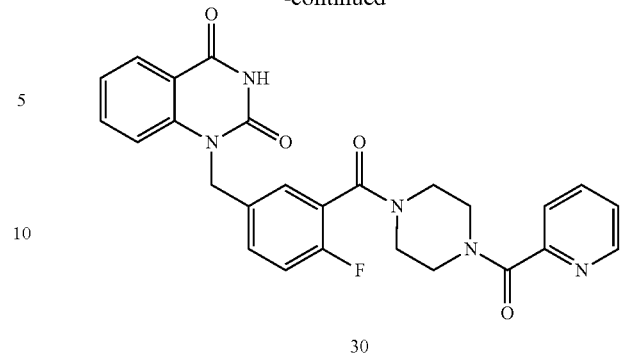 | 474 |

Example 30

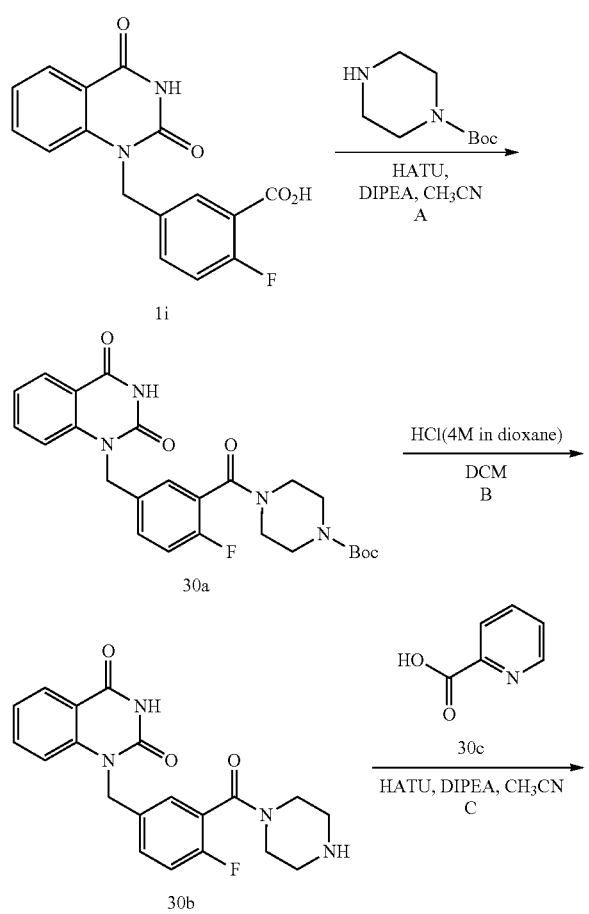

Step 30A

To a solution of 1i (107 mg, 0.34 mmol) in acetonitrile (4 mL) were added DIPEA (180 μL, 1.0 mmol), N-Boc-piperazine (76 mg, 0.408 mmol) and HATU (155 mg, 0.408 mmol). The resulting mixture was stirred at room temperature for 2 h. Saturated NH₄Cl solution was added, the mixture was extracted with EtOAc. The organic extracts were washed with brine, dried over Na₂SO₄, filtered, and concentrated. The residue was purified by silica gel chromatography to give desired product 30a (210 mg).

Step 30B

HCl (3 mL, 4M in dioxane) was added to 30a (210 mg) in DCM (2 mL). The mixture was stirred vigorously for 2 h. Solvents were removed, and the residue was dried to give white solid 30b (165 mg)

Step 30C

To a solution 30b (7 mg) in CH₃CN (0.8 mL) were added DIPEA (11 μL), 30c (2.9 mg) and HATU (9 mg). The resulting mixture was stirred at room temperature for 2 h and purified by reversed phase preparative HPLC to give title compound 30 (6.6 mg). MS (ESI): m/z=488 [M+H].

Examples 31 to 39 (Formula XI) were made from 30b and corresponding acids via the similar conditions described in step 30C of Example 30.

TABLE 3

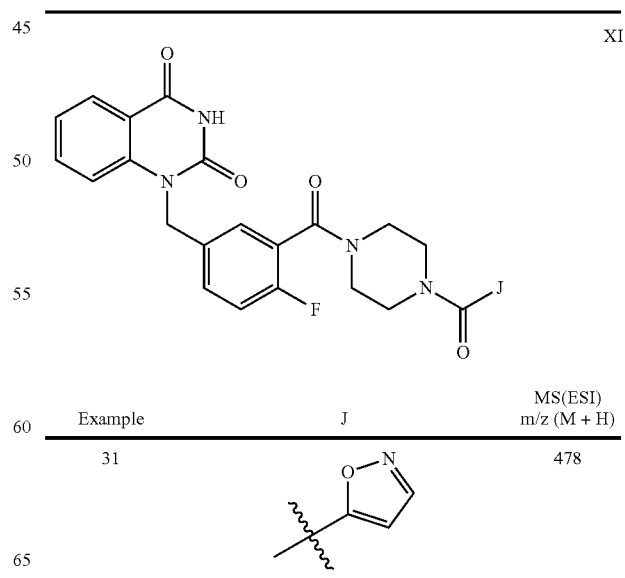

| Example | J | MS(ESI) m/z (M + H) |
|---|---|---|
| 31 | (isoxazol-5-yl) | 478 |

TABLE 3-continued
XI
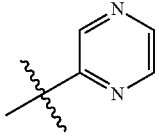 [SMILES: *c1cnccn1]
| Example | J | MS(ESI) m/z (M + H) |
|---------|---|---------------------|
| 32 | 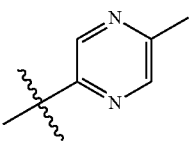 [SMILES: *c1cnc(C)cn1] | 489 |
| 33 | 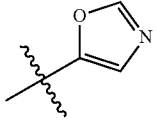 | 503 |
| 34 | 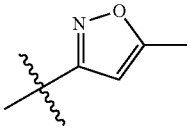 [SMILES: *c1cc(C)on1] | 478 |
| 35 | 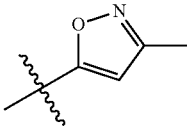 [SMILES: *c1cc(C)no1] | 492 |
| 36 | 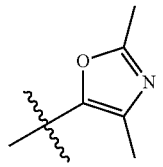 | 492 |
TABLE 3-continued
XI
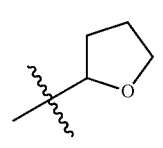 [SMILES: *C1CCCO1]
| Example | J | MS(ESI) m/z (M + H) |
|---------|---|---------------------|
| 37 | 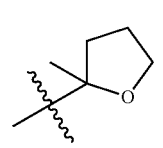 [SMILES: *C1(C)CCCO1] | 506 |
| 38 | 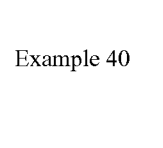 | 481 |
| 39 | | 495 |
Example 40
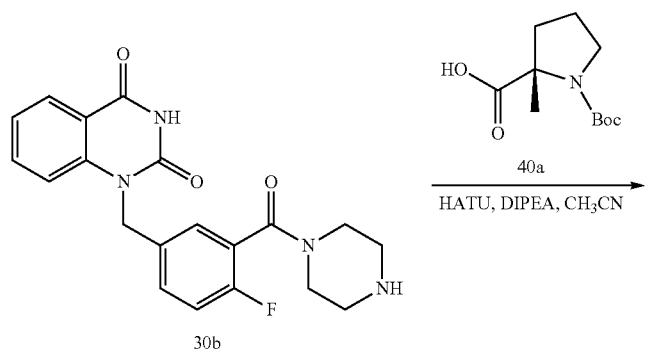

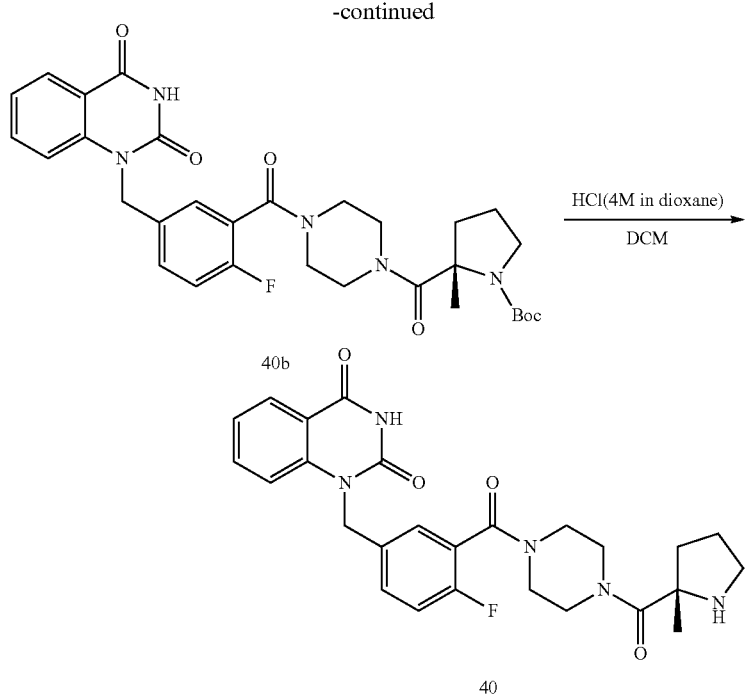

Step 40A 1-(4-fluoro-3-(piperazine-1-carbonyl)benzyl)quinazoline-2,4(1H,3H)-dione hydrochloric acid (30b, 37 mg) was suspended in acetonitrile (1.5 mL), treated with (R)-1-(tert-butoxycarbonyl)-2-methylpyrrolidine-2-carboxylic acid (40a, 30 mg), HATU (47 mg), and Et$_3$N (0.5 mL) sequentially. The reaction mixture was stirred at ambient temperature (25° C.) for 19 hrs. The reaction mixture was directly purified by flash chromatography with MeOH—CH$_2$Cl$_2$ (0-20% gradient elution) to afford the desired product, (R)-tert-butyl 2-(4-(5-((2,4-dioxo-3,4-dihydroquinazolin-1(2H)-yl)methyl)-2-fluorobenzoyl)piperazine-1-carbonyl)-2-methylpyrrolidine-1-carboxylate (40b) as the major fraction (colorless oil, 50 mg). MS (ESI): m/z=594 (M+H$^+$)

Step 40B (R)-tert-butyl 2-(4-(5-((2,4-dioxo-3,4-dihydroquinazolin-1(2H)-yl)methyl)-2-fluorobenzoyl)piperazine-1-carbonyl)-2-methylpyrrolidine-1-carboxylate (40b, 50 mg) was dissolved in CH$_2$Cl$_2$ (3 mL), treated with 4.0 N HCl in dioxane (3 mL) and stirred at ambient temperature for 2 hrs. The reaction mixture was concentrated in vacuo to afford the HCl salt of the desired product (R)-1-(4-fluoro-3-(4-(2-methylpyrrolidine-2-carbonyl)piperazine-1-carbonyl)benzyl)quinazoline-2,4(1H,3H)-dione as tan solid (40, 37 mg). MS (ESI): m/z=494 (M+H$^+$).

Example 41

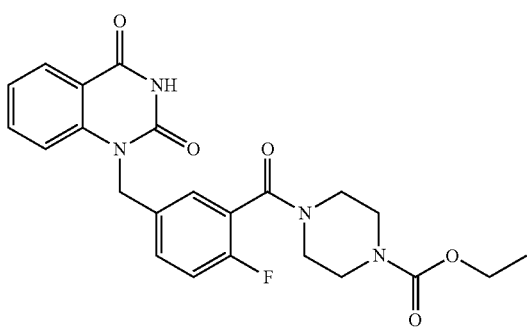

41

To a solution of 30b (7.7 mg) in DCM (0.8 mL) were added Et$_3$N (6 µL) and ethyl chloroformate (3 µL). The mixture was stirred for 16 h and purified by reversed phase prep HPLC to give title compound 41 (6.0 mg). MS (ESI): m/z=455 [M+H].

Example 42

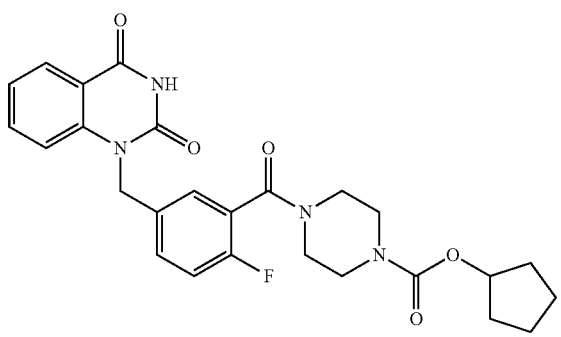

42

The title compound was made from 30b and cyclopentyl chloroformate via the similar conditions described in Example 41. MS (ESI): m/z=495 [M+H].

Example 43

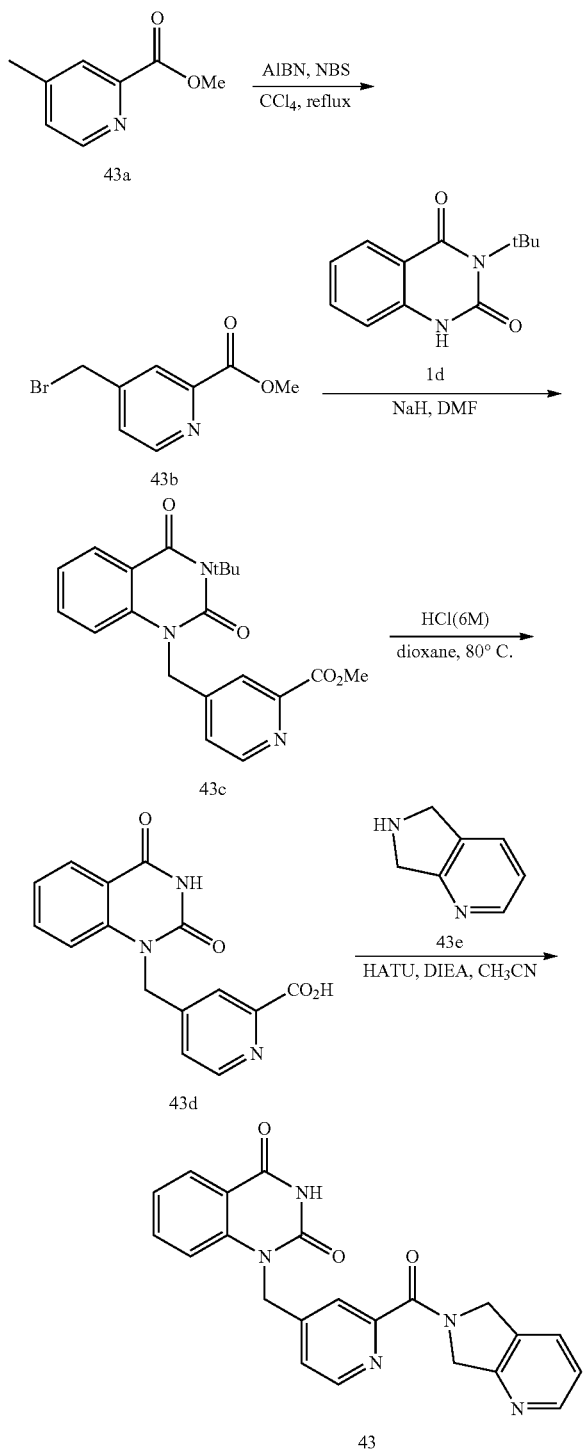

Step 43A
A mixture of 43a (426 mg, 2.8 mmol), NBS (555 mg, 3.1 mmol) and AIBN (277 mg, 1.69 mmol) in $CCl_4$ (15 mL) was refluxed under $N_2$ for 5 h. The solvents were removed and the residue was suspended with ether. The solid was filtered off. The filtrate was concentrated and purified by silica gel chromatography to give desired product 43b (46 mg).

Step 43B
To a solution of 1d (39 mg, 0.18 mmol) in DMF (2 mL) in ice bath was added 60 wt % NaH (8 mg, 0.198 mmol). The solution was stirred for 30 min and bromide 43b (45 mg, 0.198 mmol) was added. The mixture was allowed to warm to room temperature and stirred for 2 h. Saturated $NH_4Cl$ solution was added to quench the reaction. The reaction mixture was extracted with EtOAc. The organic extracts were washed with brine, dried over $Na_2SO_4$, filtered and concentrated. The residue was purified by silica gel chromatography to give desired product 43c (29 mg).

Step 43C
A solution of 43c (29 g) and 6M HCl (1 mL) in dioxane (1.5 mL) was refluxed 24 h. The mixture was dried in vacuum to give beige solid 43d (20 mg).

Step 43D
To a solution of 43d (9.4 mg, 0.03 mmol) in acetonitrile (0.8 mL) were added DIPEA (18 μL, 0.1 mmol), 43e (5.6 mg, 0.036 mmol) and HATU (13.7 mg, 0.036 mmol). The resulting mixture was stirred at room temperature for 2 h and purified by reversed phase preparative HPLC to give title compound 43 (8.5 mg). MS (ESI): m/z=418 [M+H].

Example 44

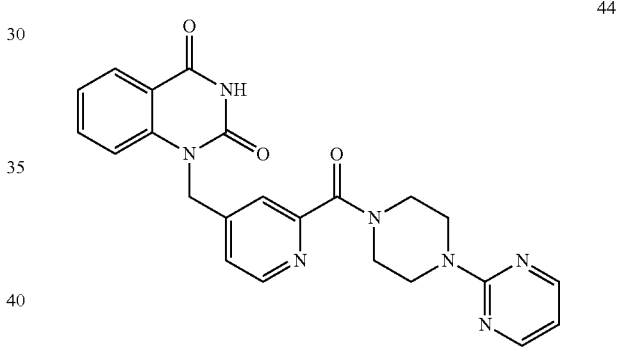

The title compound was made from acid 43d and the corresponding amine via the similar conditions described in step 43D of Example 43. MS (ESI): m/z=444 [M+H].

Biological Testing

PARP-1 Activity Assay:

PARP-1 activity was determined using a HT Universal chemiluminescent PARP Assay Kit (Trevigen, Gaithersburg, Md., USA). The assay was to measure the incorporation of biotinylated poly(ADP-ribose) onto histone proteins catalyzed by PARP-1 upon activation with DNA. Experimental procedures were followed according to the instruction provided with the assay kit. In brief, PARP-1 (0.5 unit/well) was incubated with activated DNA and $NAD^+$ in reaction buffer in the presence or absence of test articles in histone-coated strip wells at 25° C. for 45 minutes. After incubation, the strip wells were incubated with Strep-HRP at 25° C. for 60 minutes after washes with PBS containing 0.1% Triton X-100. The chemiluminescence was measured with a Victor X5 2030 Multilabel Reader (Perkin Elmer) immediately after the addition of PeroxyGlow™ to the strip wells. IC50 value was calculated using median-effect method (Chou, T. C. (2006). Pharmacol. Rev. 58(3): 621-681). The IC50 value for the example compounds is shown in Table 4, ranging from 0.001 to 0.05 μM.

Cell Proliferation Assay:

MDA-MB-436 cells were purchased from American Type Culture Collection (USA). Cells were maintained at 37° C. in a humidified atmosphere with 5% $CO_2$. For proliferation test, MDA-MB-436 cells were seeded in 96-well plates at low density in RPMI-1640 medium supplemented with 10% FBS and incubated for 24 h at 37° C. in a humidified atmosphere with 5% $CO_2$. Cells were further incubated in fresh medium in the presence or absence of the test articles at 37° C. for 7 days. The proliferation of cells was measured with a 3-(4,5-dimethylthiazol-2-yl)-5-(3-carboxymethoxyphenyl)-2-(4-sulfophenyl)-2H-tetrazolium (MTS) assay using a CellTiter 96® Aqueous Non-Radioactive Cell Proliferation kit (Promega). The absorbance at 490 nm ($A_{490}$) was determined with a Victor X5 2030 Multilabel Reader (Perkin Elmer). $IC_{50}$ value was calculated using median-effect method (Chou, T. C. (2006). Pharmacol. Rev. 58(3): 621-681). The compounds of present invention exhibit an $IC_{50}$ value of 0.1 nM to 10 μM in the cellular assay.

Pharmacokinetic Assay:

The tested articles were given to Sprague-Dawley rats by intravenous and oral administration. Plasma samples were prepared from blood samples which were collected at various time points. The plasma concentrations of the tested articles were determined by specific LC-MS/MS analytical methods. Pharmacokinetic parameters were calculated with WinNonlin®. Examples 25, 27, 38 were bioavailable with a t½>2 hour after oral administrations in rats.

In Vivo Efficacy Study:

The in vivo potentiating antitumor activity was assessed with SW620 xenograft mice treated with temozolomide. Xenograft was developed in athymic mice (nude mouse) with SW620 cells. In brief, SW620 cells ($5 \times 10^6$ in 100 μL) were implanted s.c. into the hind flank region of each mouse and allowed to grow to the designated size (c.a. 200-300 $mm^3$) before treatment. The tested articles were given orally at various dose levels in combination with temozolomide (50 mg/kg) once daily for 5 consecutive days. Tumor and body weight were measured during the experiments, and tumor volumes were estimated from the formula [length/2]×[width$^2$]. Established tumors in each animal were individually normalized to their size at the start of the experiment, and the data were calculated as the change in tumor volume relative to the day 0 volume by the use of the relative tumor volume (RTV) formula, $RTV=TV_x/TV_0$, where $TV_x$ is the tumor volume on any day and $TV_0$ is the tumor volume at the initiation of dosing. Significant suppression of tumor growth was observed with examples 25, 27, 38 compared to the temozolomide control.

TABLE 4

| | Testing Results | |
|---|---|---|
| Example | PARP1 enzyme $IC_{50}$ (μM) | MDA-MB-436 cells $EC_{50}$ (μM) |
| 1 | A | B |
| 2 | A | C |
| 3 | A | C |
| 4 | B | C |
| 5 | B | C |
| 6 | B | C |
| 7 | A | C |
| 8 | A | B |
| 9 | A | B |
| 10 | A | B |
| 11 | A | C |
| 12 | A | A |
| 13 | A | B |
| 14 | A | B |
| 15 | A | C |
| 16 | A | C |
| 17 | A | B |
| 18 | A | C |
| 19 | B | C |
| 20 | B | Not determined |
| 21 | B | C |
| 22 | B | Not determined |
| 23 | A | B |
| 24 | A | B |
| 25 | A | B |
| 26 | A | B |
| 27 | A | B |
| 28 | A | A |
| 29 | A | C |
| 30 | A | B |
| 30b | A | Not determined |
| 31 | A | B |
| 32 | A | B |
| 33 | A | B |
| 34 | A | B |
| 35 | A | B |
| 36 | A | B |
| 37 | A | B |
| 38 | A | B |
| 39 | A | B |
| 40 | A | B |
| 41 | A | B |
| 42 | A | B |
| 43 | A | B |

0.0001 μM < A ≤ 0.01 μM;
0.01 μM < B ≤ μM;
1 μM < C < 100 μM

Many modifications and other embodiments of the present disclosure will come to mind to one skilled in the art to which the present disclosure pertains having the benefit of the teachings presented in the foregoing description. It will be apparent to those skilled in the art that variations and modifications of the present disclosure may be made without departing from the scope or spirit of the present disclosure. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A compound of formula (I), or a pharmaceutically acceptable salt thereof:

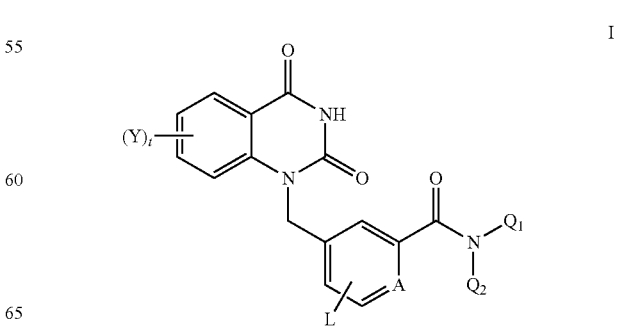

wherein:
A is CR$^a$; wherein R$^a$ is selected from the group consisting of hydrogen, halogen, and unsubstituted or substituted alkyl;
L is selected from the group consisting of hydrogen, halogen, cynao, nitro, unsubstituted or substituted alkyl, and unsubstituted or substituted alkoxyl;
Q$^1$ and Q$^2$ are independently selected from the group consisting of hydrogen, unsubstituted or substituted alkyl, unsubstituted or substituted alkenyl, unsubstituted or substituted alkynyl, unsubstituted or substituted cycloalkyl, unsubstituted or substituted cycloalkenyl, unsubstituted or substituted heterocycloalkyl, unsubsituted or substituted aryl, and unsubstituted or substituted heteroaryl; or Q$^1$ and Q$^2$ together with the nitrogen atom to which they are attached may form cyclic moiety selected from the group consisting of unsubstituted or substituted heterocycloalkyl, unsubstituted or substituted heterocycicoalkenyl, and unsubstituted or substituted heteroaryl;
each Y is independently selected from the group consisting of hydrogen, halogen, cyano, nitro, unsubstituted or substituted alkyl, OR$^1$, and NR$^1$R$^2$;
wherein R$^1$ and R$^2$ are independently selected from the group consisting of hydrogen, unsubstituted or substituted alkyl, unsubstituted or substituted alkenyl, unsubstituted or substituted alkynyl, unsubstituted or substituted cycloalkyl, unsubstituted or substituted cycloalkenyl, and unsubstituted or substituted heterocycloalkyl; and
t=0, 1, or 2.

2. A compound of formula (II), or a pharmaceutically acceptable salt thereof:

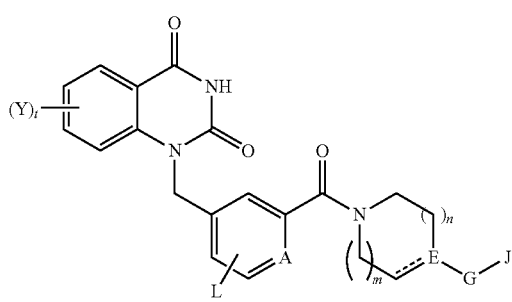

II wherein:
A is CR$^a$; wherein R$^a$ is selected from the group consisting of hydrogen, halogen, and unsubstituted or substituted alkyl;
L is selected from the group consisting of hydrogen, halogen, cyano, nitro, unsubstituted or substituted alkyl, and unsubstituted or substituted alkoxyl;
each Y is independently selected from the group consisting of hydrogen, halogen, cyano, nitro, unsubstituted or substituted alkyl, OR$^1$, and NR'R$^2$; wherein R$^1$ and R$^2$ are independently selected from the group consisting of hydrogen, unsubstituted or substituted alkyl, unsubstituted or substituted alkenyl, unsubstituted or substituted alkynyl, unsubstituted or substituted cycloalkyl, unsubstituted or substituted cycloalkenyl, and unsubstituted or substituted heterocycloalkyl;
E is N or CR$^3$; wherein R$^3$ is absent, or R$^3$ is selected from the group consisting of hydrogen, halogen, ad unsubstituted or substituted alkyl;
G is absent, or G is selected from the group consisting of unsubstituted or substituted alkyl, O, C(O), C(O)O, O(CO)NH, —O—N═, (CO)NH, NH, NH(CO), NH(CO)O, S, SO$_2$, (SO$_2$)NH, and NH(SO$_2$);
J is absent, or J is selected from the group consisting of hydrogen, halogen, cyano, nitro, hydroxyl, unsubstituted or substituted alkoxy, unsubstituted or substituted alkyl, unsubstituted or substituted alkenyl, unsubstituted or substituted alkynyl, unsubstituted or substituted cycloalkyl, unsubstituted or substituted cycloalkenyl, unsubstituted or substituted heterocycloalkyl, unsubstituted or substituted aryl, and unsubstituted or substituted heteroaryl;
═══ denotes a carbon-carbon single or double bond; and
t, m and n are each independently selected from the integer of 0, 1, and 2.

3. The compound of claim 2, wherein E is CR$^3$, CR$^3$, G and J together form a spiro C$_3$-C$_7$ cycloalkyl or heterocyclic group.

4. The compound of claim 2, wherein Y is hydrogen; L is hydrogen; A is selected from the group consisting of CH, N, CF and CCl; m is 0 or 1; n is 0 or 1.

5. The compound of claim 2, wherein E is N or CR$^3$; G is absent, or G is selected from the group consisting of O, C(O), C(O)O, C(O)NH, O(CO)NH, and O—N═.

6. The compound of claim 2, wherein J is selected from the group consisting of hydrogen, halogen, hydroxyl, unsubstituted or substituted C$_{3-6}$ cycloalkyl, unsubstituted or substituted C$_{1-4}$ alkoxyl, unsubstituted or substituted C$_{1-4}$ alkyl, unsubstituted or substituted phenyl, unsubstituted or substituted pyridinyl, unsubstituted or substituted pyrroidinyl, unsubstituted or substituted piperazinyl, unsubstituted or substituted pyrazole, unsubstituted or substituted imidazole, unsubstituted or substituted indoline, unsubstituted or substituted pyrimidinyl, unsubstituted or substituted oxazole, unsubstituted or substituted isoxazole, unsubstituted or substituted pyrazinyl, and unsubstituted or substituted tetrahydrofuran.

7. The compound of claim 2, which is selected from the group consisting of:

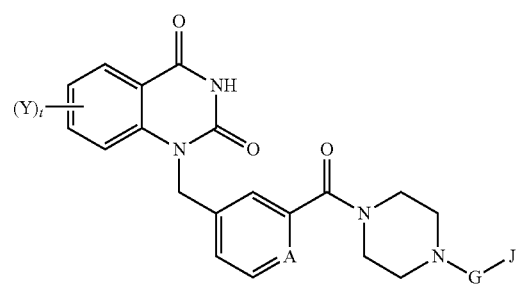

IV

-continued

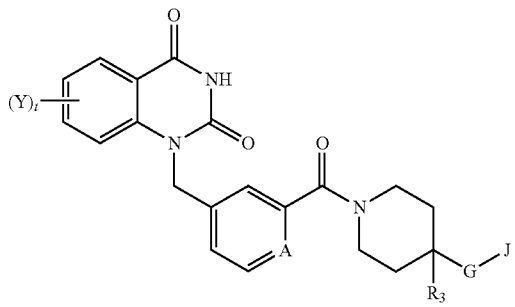

V

8. The compound of claim 2, which is of formula (VII)

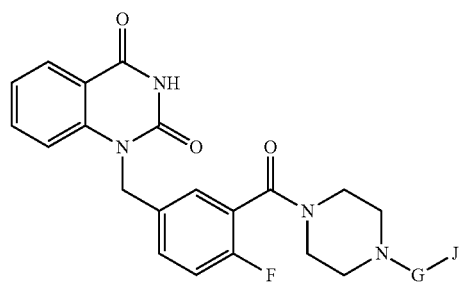

VII wherein G is absent or C(O); J is selected from the group consisting of unsubstituted or substituted cycloalkyl, unsubstituted or substituted heterocycloalkyl, unsubstituted or substituted aryl, and unsubstituted or substituted heteroaryl.

9. The compound of claim 8, wherein G is absent; and wherein J is selected from the group consisting of: unsubstituted or substituted phenyl, unsubstituted or substituted pyridinyl, unsubstituted or substituted pyrrolidinyl, unsubstituted or substituted piperazinyl, unsubstituted or substituted pyrazole, unsubstituted or substituted imidazole, unsubstituted or substituted indoline, unsubstituted or substituted pyrimidinyl, unsubstituted or substituted oxazole, unsubstituted or substituted isoxazole, and unsubstituted or substituted pyrazinyl.

10. The compound of claim 8, wherein G is C(O); and wherein J is selected from the group consisting of:

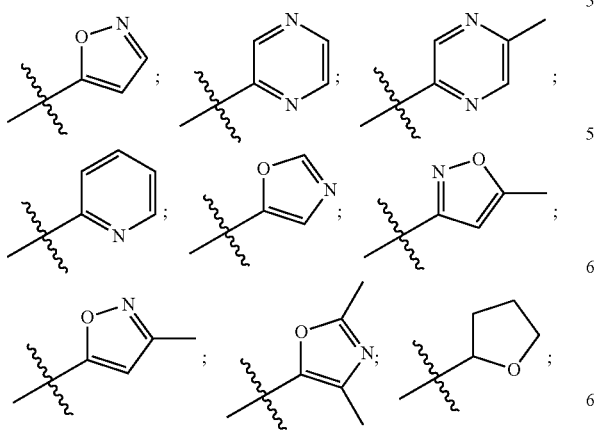

-continued

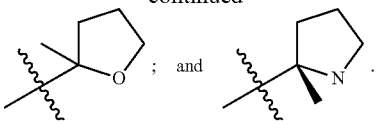

11. The compound of claim 2, which is of formula (VIII)

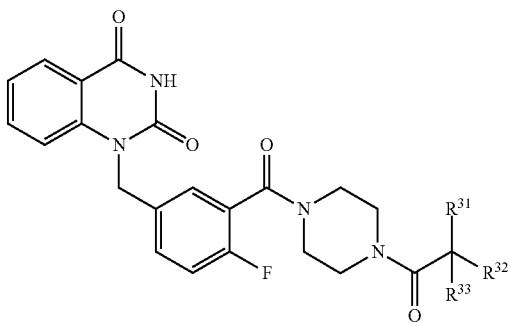

VIII wherein $R^{31}$, $R^{32}$, and $R^{33}$ are each independently selected from the group consisting of hydrogen, halogen, and unsubstituted or substituted alkyl; or $R^{31}$ and $R^{32}$ may combine with an atom or atoms to which they are attached to form a cyclic moiety selected from the group consisting of unsubstituted or substituted cycloalkyl, and unsubstituted or substituted heterocycloalkyl.

12. The compound of claim 2, which is of formula (IX):

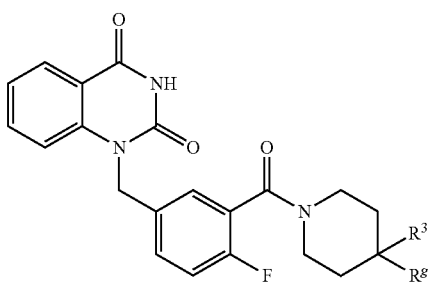

IX wherein $R^3$ is hydrogen or halogen; and
wherein $R^8$ is selected from the group consisting of hydrogen, F, —OH, hydroxyl, —OEt, —OiPr, —OtBu, —OCHF$_2$,

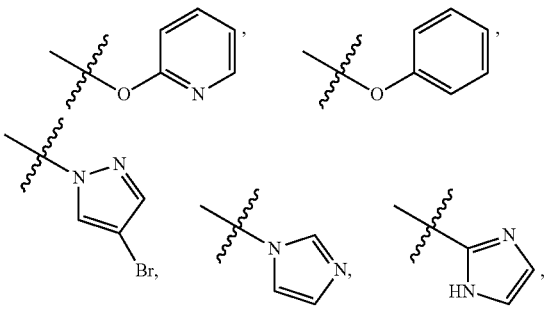

-continued

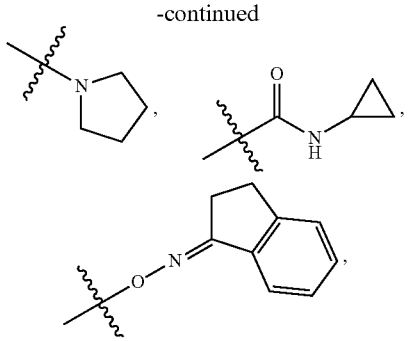

—C(O)OMe, —C(O)OH, and —OC(O)NHEt.

13. A compound, or a pharmaceutically acceptable salt thereof, represented by formula (III):

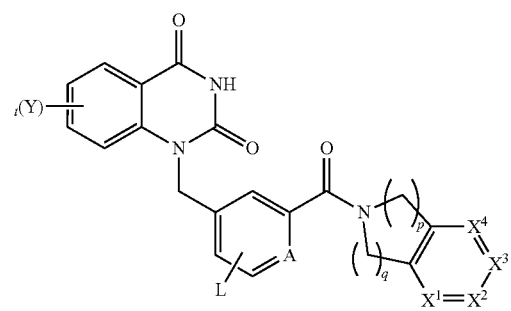

III wherein A is $CR^a$; wherein $R^a$ is selected from the group consisting of hydrogen, halogen, and unsubstituted or substituted alkyl;

L is selected from the group consisting of hydrogen, halogen, cyano, nitro, unsubstituted or substituted alkyl, and unsubstituted or substituted alkoxyl;

each Y is independently selected from the group consisting of hydrogen, halogen, cyano, nitro, unsubstituted or substituted alkyl, $OR^1$, and $NR^1R^2$;

wherein $R^1$ and $R^2$ are independently selected from the group consisting of hydrogen, unsubstituted or substituted alkyl, unsubstituted or substituted alkenyl, unsubstituted or substituted alkynyl, unsubstituted or substituted cycloalkyl, unsubstituted or substituted cycloalkenyl, and unsubstituted or substituted heterocycloalkyl;

each of $X^1$, $X^2$, $X^3$ and $X^4$ are independently selected from the group consisting of N and $CR^4$;

wherein $R^4$ is selected from the group consisting of hydrogen, halogen, cyano, nitro, unsubstituted or substituted alkyl, unsubstituted or substituted alkenyl, unsubstituted or substituted alkynyl, unsubstituted or substituted cycloalkyl, unsubstituted or substituted cycloalkenyl, unsubstituted or substituted heterocycloalkyl, unsubstituted or substituted aryl, unsubstituted or substituted heteroaryl, $OR^5$, $(CO)R^5$, $(CO)OR^5$, $(CO)NHR^5$, $NHR^5$, $NH(CO)R^5$, $NH(CO)OR^5$, $NH(CO)NHR^5$, $SO_2R^5$, $(SO_2)OR^5$, and $SO_2NHR^5$;

wherein $R^5$ is selected from the group consisting of hydrogen, unsubstituted or substituted alkyl, unsubstituted or substituted alkenyl, unsubstituted or substituted alkynyl, unsubstituted or substituted cycloalkyl, unsubstituted or substituted cycloalkenyl, unsubstituted or substituted heterocycloalkyl, unsubstituted or substituted aryl, and unsubstituted or substituted heteroaryl;

t=0, 1, or 2;

p=1, or 2; and q=1, or 2.

14. The compound of claim 13, represented by formula (VI):

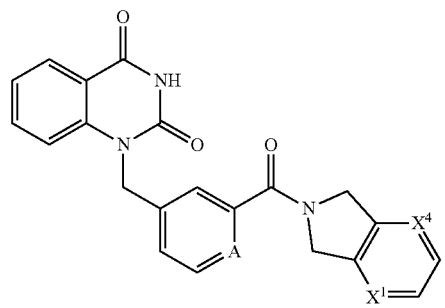

VI

15. The compound of claim 1, or a pharmaceutically acceptable salt thereof, which is selected from the group consisting of:

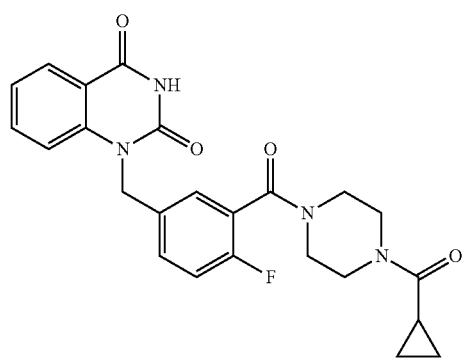

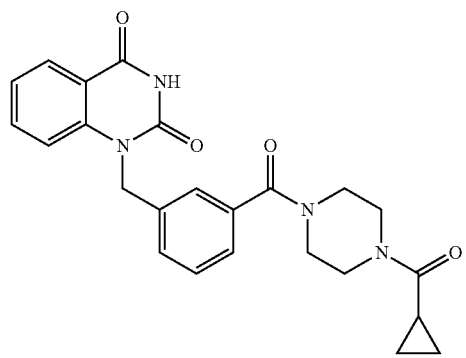

51
-continued
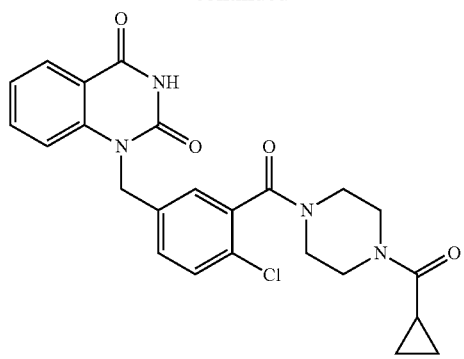
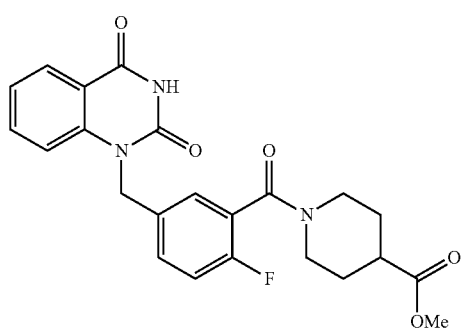
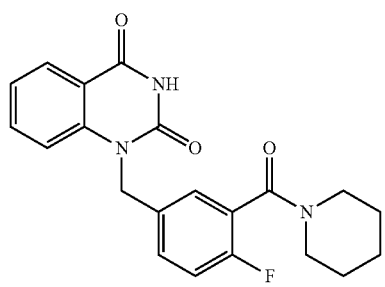
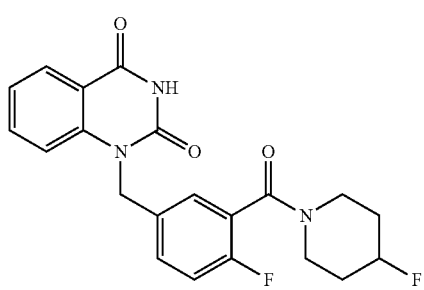
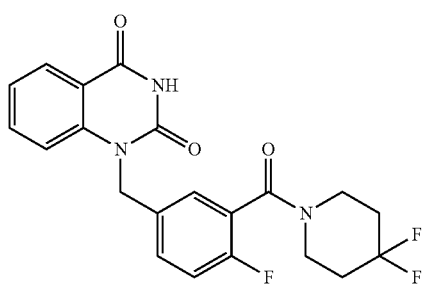
52
-continued
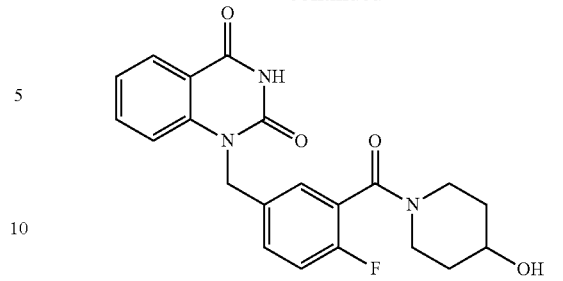
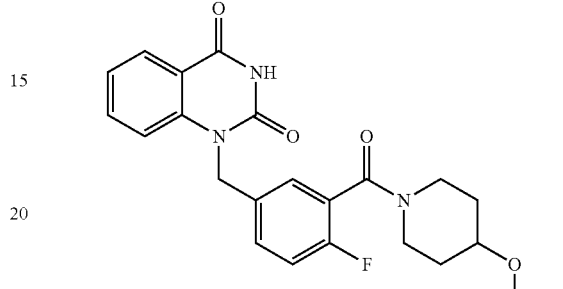
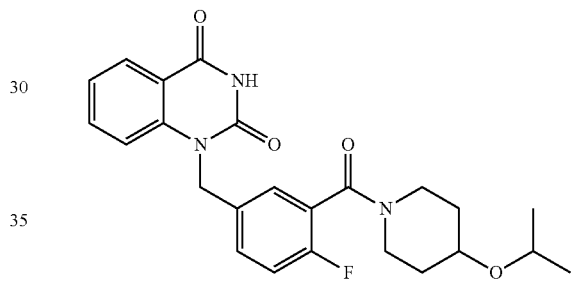
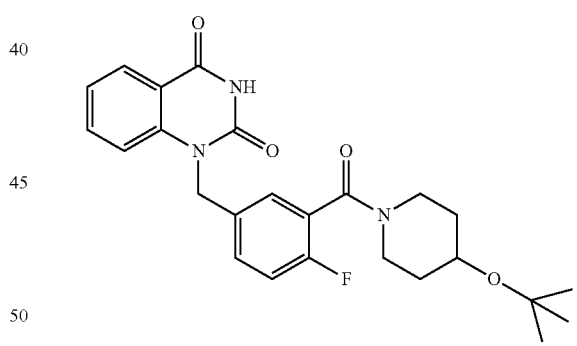
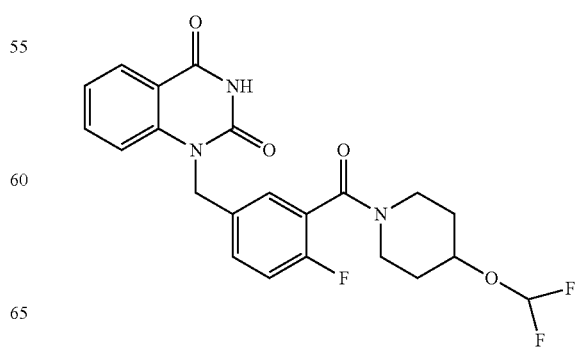

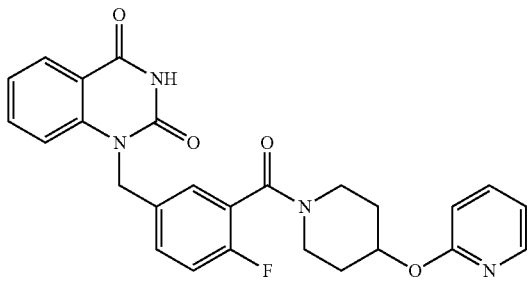
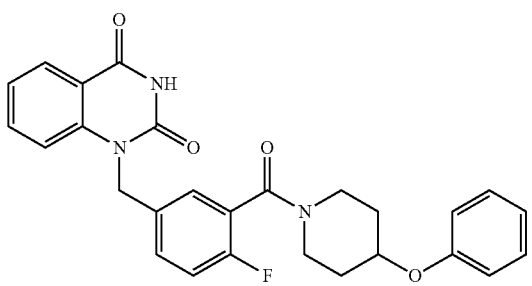
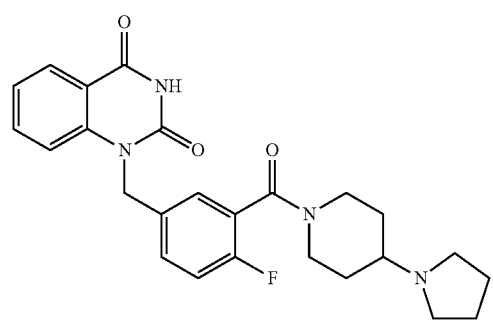
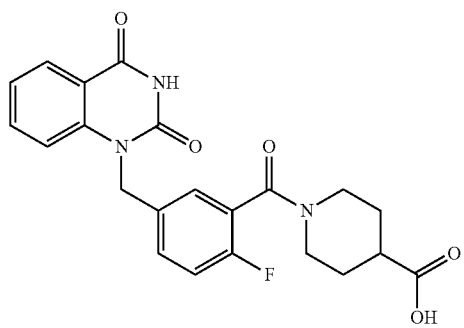
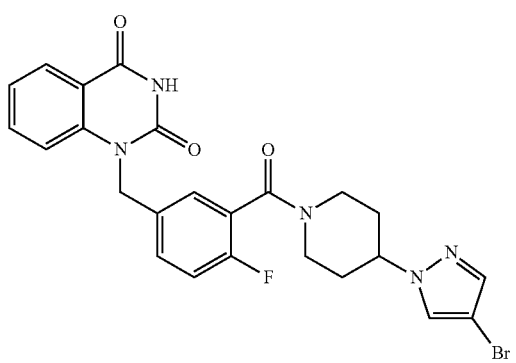
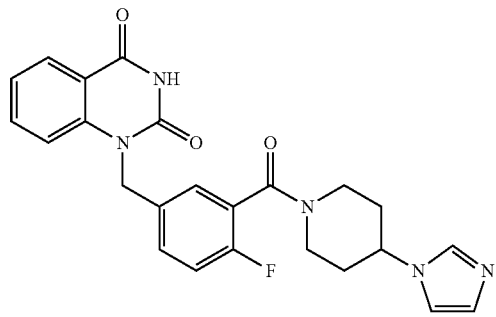
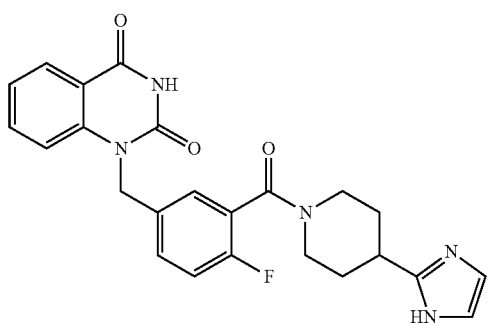
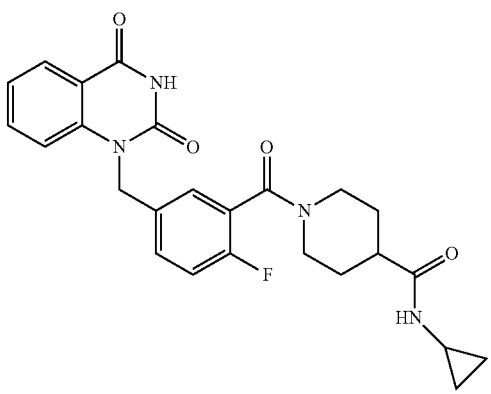
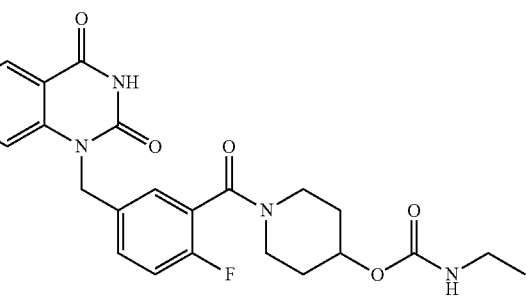
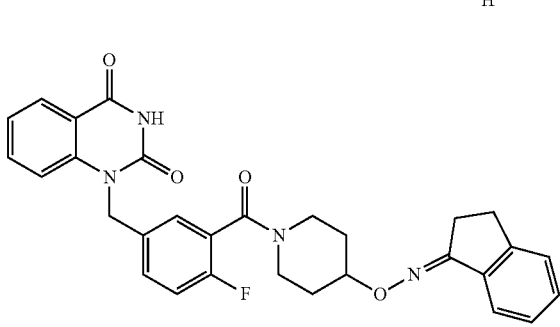

55
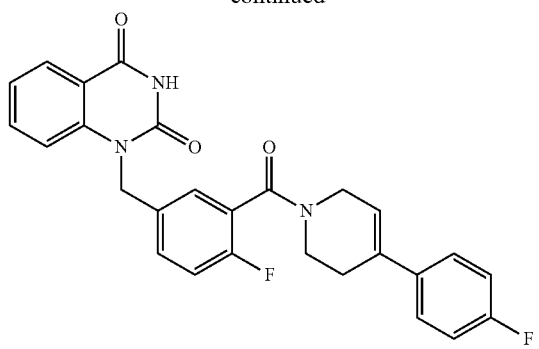
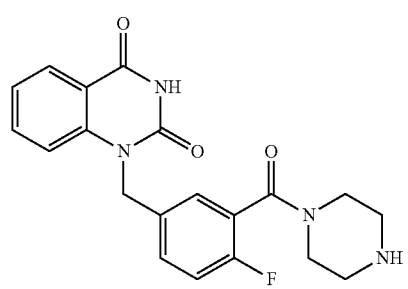
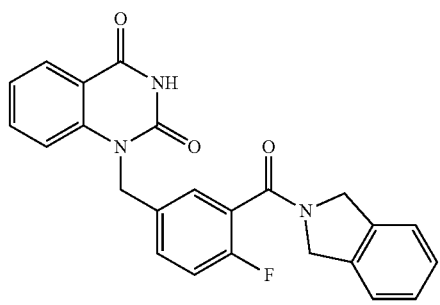
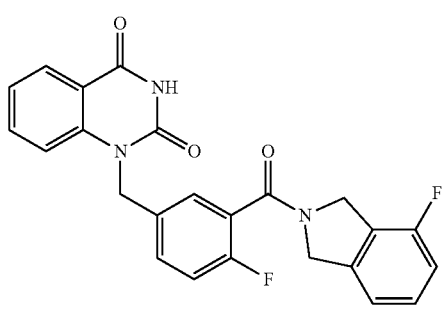
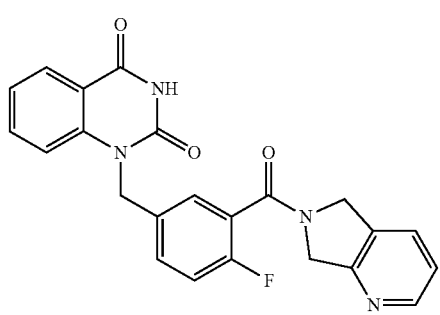
56
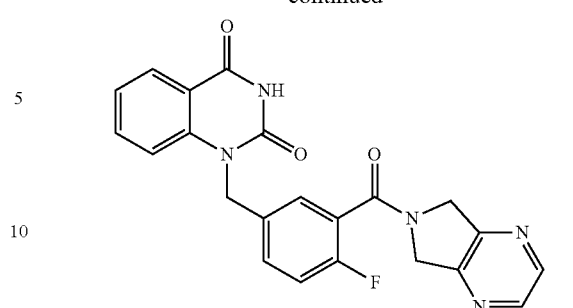
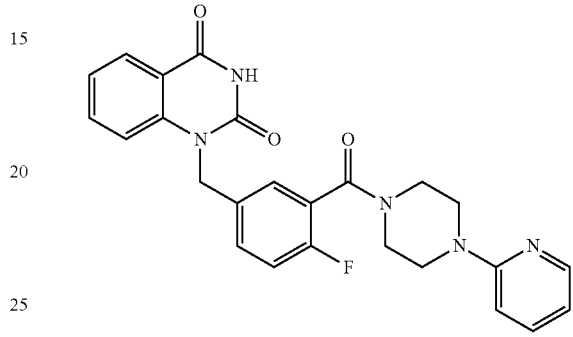
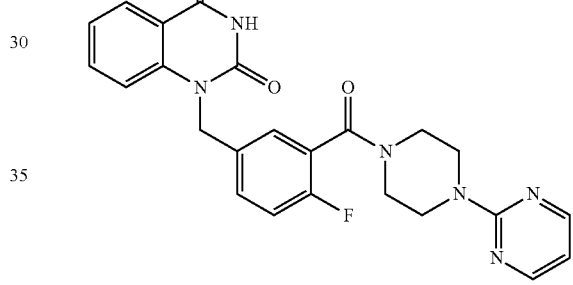
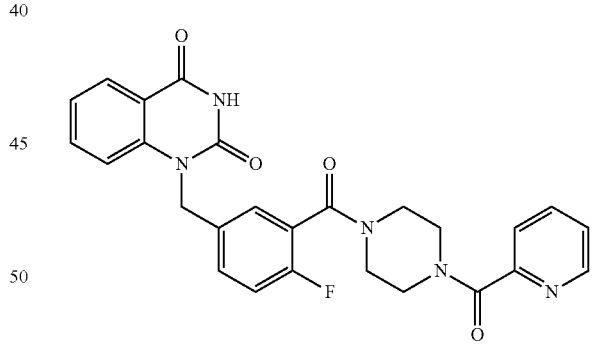
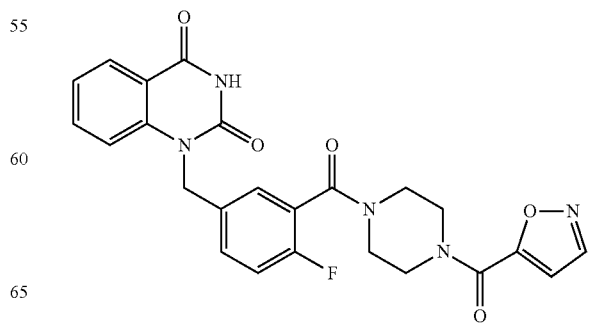

57
-continued
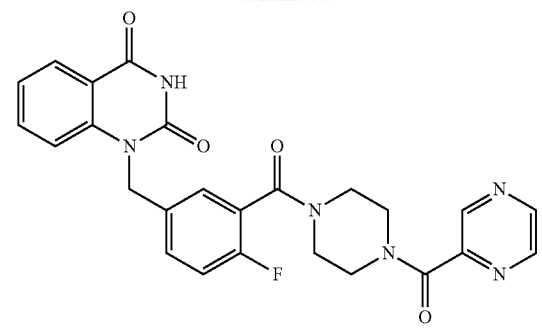
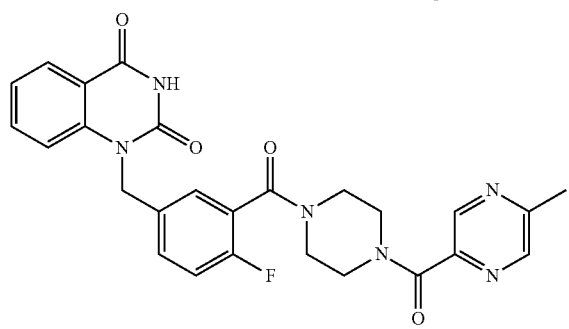
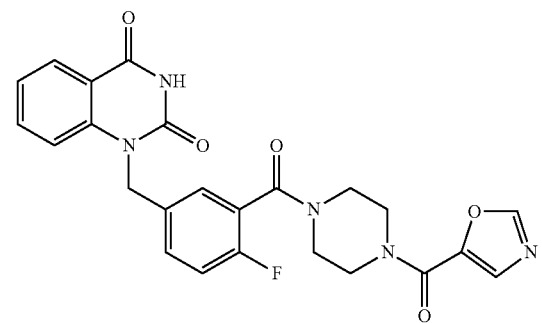
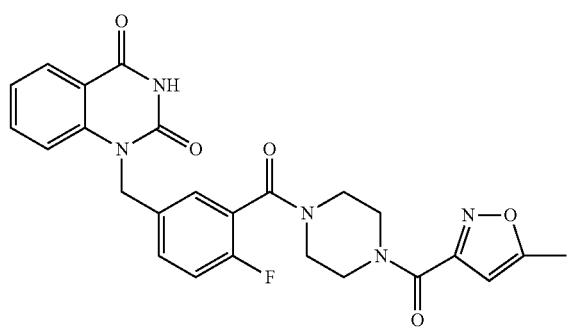
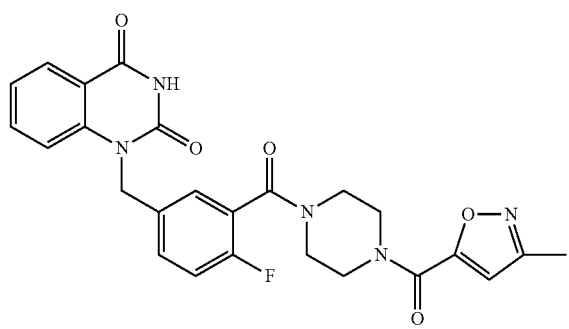
58
-continued
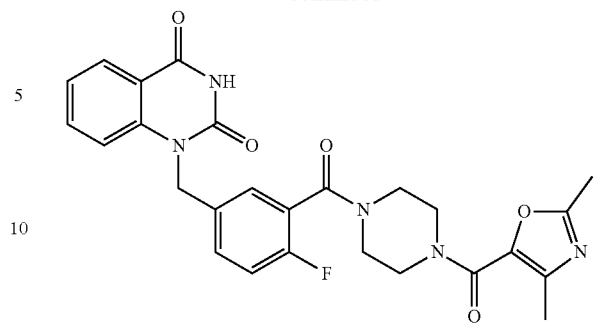
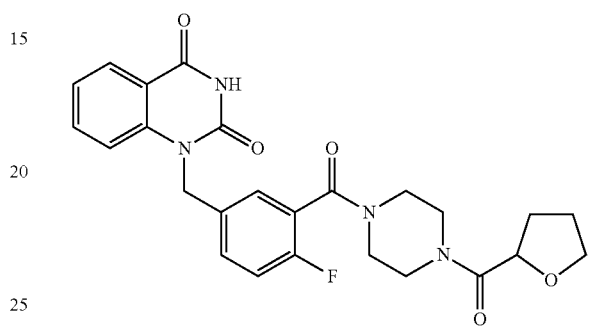
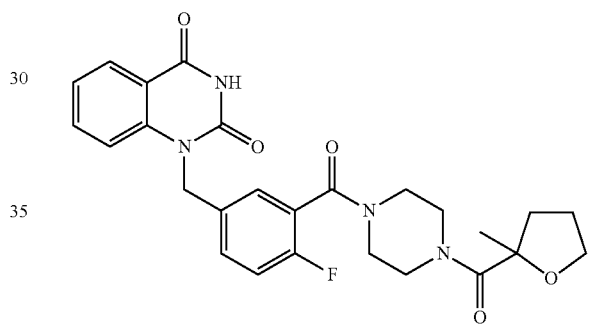
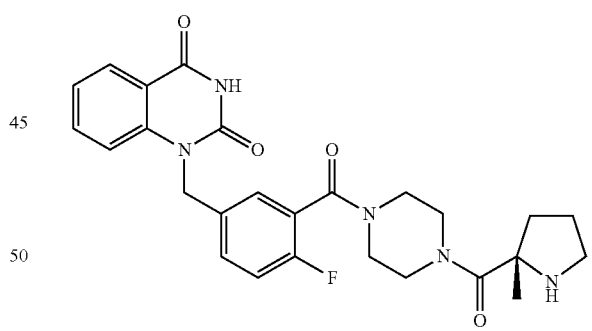
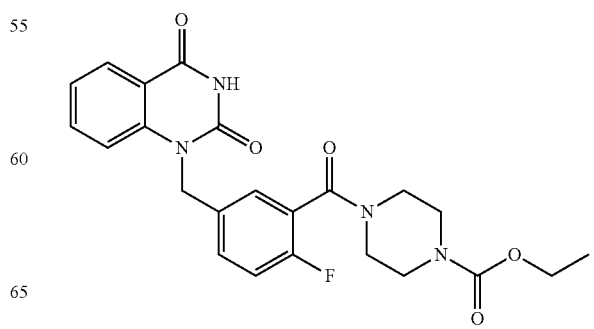

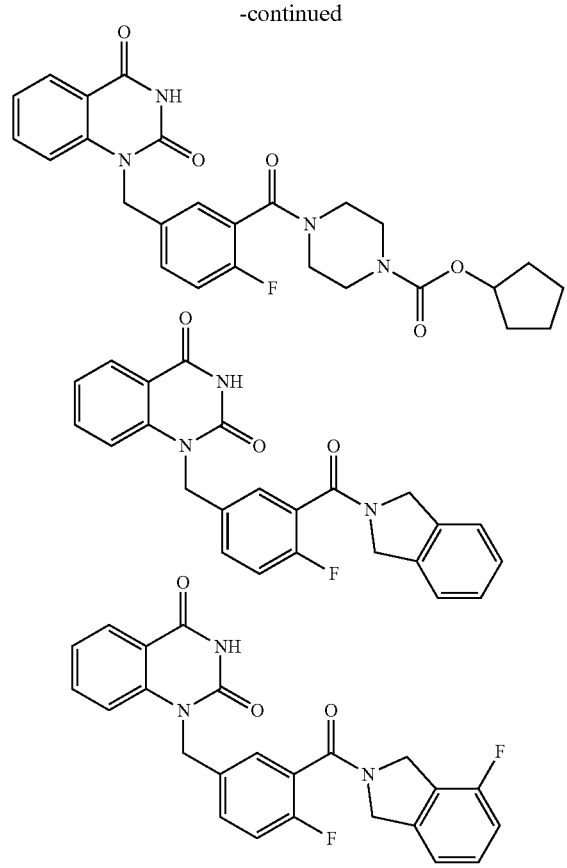
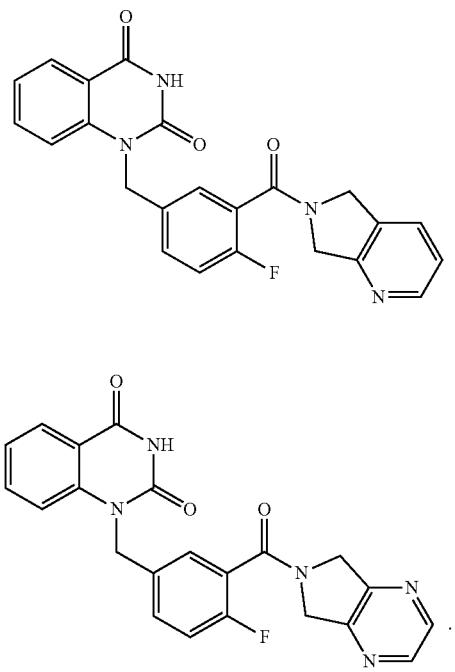
16. A pharmaceutical composition comprising the compound of claim 1, and a pharmaceutically acceptable carrier.
* * * * *

UNITED STATES PATENT AND TRADEMARK OFFICE
CERTIFICATE OF CORRECTION

| | | |
|---|---|---|
| PATENT NO. | : 9,090,568 B2 | Page 1 of 2 |
| APPLICATION NO. | : 14/004633 | |
| DATED | : July 28, 2015 | |
| INVENTOR(S) | : Liu et al. | |

It is certified that error appears in the above-identified patent and that said Letters Patent is hereby corrected as shown below:

On page 2 of the title page, left column, second line from the bottom, change "DL-3-Carboxy-4methexyphenylalanine" to -- DL-3-Carboxy-4-methoxyphenylalanine --.

In the specification,
At column 3, line 17, delete "A is selected from the group consisting of" and insert therefor -- A is --;
    line 40, change "$NR^1, R^{2}$" to -- $NR^1R^2$ --.

At column 4, line 18, change "$CR^3, CR^3$, G and J" to -- $CR^3; CR^3$, G and J --; and
    line 44, change "consisting N" to -- consisting of N --.

At column 5, line 47, change "idenyl" to -- indenyl --.

At column 14, line 59, delete "A is selected from the group consisting of" and insert therefor -- A is --.

At column 15, line 13, change "$NR^1, R^{2}$" to -- $NR^1R^2$ --.

At column 16, line 46, change "consisting N" to -- consisting of N --.

At column 17, line 62, change "alkyl, 0" to -- alkyl, O --.

At column 20, line 2, change "$R^9$" to -- $R^g$ --;
    line 8, change "$R^9$" to -- $R^g$ --; and
    line 9, delete "hydroxyl,".

At column 27, after the heading "Example 1," change the label of the first structure from "1e" to -- 1a --.

At column 42, line 13, change "A solution of 43c (29 g)" to -- A solution of 43c (29 mg) --.

Signed and Sealed this
Fifth Day of January, 2016

Michelle K. Lee
*Director of the United States Patent and Trademark Office*

CERTIFICATE OF CORRECTION (continued)
U.S. Pat. No. 9,090,568 B2

In the claims,
In claim 1, at column 45, line 6, change "cynao" to -- cyano --; and
at column 45, lines 21-22, change "heterocycicoalkenyl" to -- heterocycloalkenyl --.

In claim 2, at column 45, line 63, change "NR'R$^2$" to -- NR$^1$R$^2$ --; and
at column 46, line 5, change "halogen ad" to -- halogen and --.

In claim 3, at column 46, line 26, change "CR$^3$, CR$^3$, G and J" to -- CR$^3$; CR$^3$, G and J --.

In claim 6, at column 46, line 43, change "pyrroidinyl" to -- pyrrolidinyl --.

In claim 7, at column 47, please place a "." at the end of the claim.

In claim 12, at column 48, line 51, change "R$^8$" to -- R$^g$ --; and
line 52, delete "hydroxyl,".

In claim 14, at column 50, insert a -- . -- at the end of the claim.